US010165987B2

(12) United States Patent
Cales

(10) Patent No.: US 10,165,987 B2
(45) Date of Patent: Jan. 1, 2019

(54) METHOD FOR DISPLAYING MEDICAL IMAGES

(71) Applicants: CENTRE HOSPITALIER UNIVERSITAIRE D'ANGERS, Angers (FR); UNIVERSITE D'ANGERS, Angers (FR)

(72) Inventor: Paul Cales, Avrille (FR)

(73) Assignees: CENTRE HOSPITALIER UNIVERSITAIRE D'ANGERS, Angers (FR); UNIVERSITE D'ANGERS, Angers (FR)

( * ) Notice: Subject to any disclaimer, the term of this patent is extended or adjusted under 35 U.S.C. 154(b) by 0 days.

(21) Appl. No.: 15/500,601

(22) PCT Filed: Jul. 31, 2015

(86) PCT No.: PCT/EP2015/067746
§ 371 (c)(1),
(2) Date: Jan. 31, 2017

(87) PCT Pub. No.: WO2016/016458
PCT Pub. Date: Feb. 4, 2016

(65) Prior Publication Data
US 2017/0215814 A1    Aug. 3, 2017

(30) Foreign Application Priority Data

Aug. 1, 2014    (EP) .................................. 14179587

(51) Int. Cl.
*G06K 9/00*    (2006.01)
*A61B 5/00*    (2006.01)
(Continued)

(52) U.S. Cl.
CPC ............ *A61B 5/743* (2013.01); *A61B 5/0095* (2013.01); *A61B 5/015* (2013.01);
(Continued)

(58) Field of Classification Search
CPC ...... A61B 5/743; A61B 5/4244; A61B 5/0095; A61B 5/015; A61B 5/04008; A61B 6/032;
(Continued)

(56) References Cited

U.S. PATENT DOCUMENTS

2006/0056691 A1    3/2006   Vaz
2006/0110358 A1    5/2006   Hsu
(Continued)

FOREIGN PATENT DOCUMENTS

EP    2120208        11/2009
EP    2120208 A1 *  11/2009    ............... G06T 7/00
(Continued)

OTHER PUBLICATIONS

Moal et al. "Fractal dimension can distinguish models and pharmacologic changes in liver fibrosis in rats" Hepatology, 2002, 36(4):840-849.
(Continued)

*Primary Examiner* — Gregory F Cunningham
(74) *Attorney, Agent, or Firm* — Young & Thompson

(57) ABSTRACT

A method for displaying at least two medical images, each medical image highlighting at least one feature, including steps of obtaining a 2D medical image, identifying at least two features on the obtained medical image, generating masks showing the identified features, each mask highlighting at least one of the identified features, generating a set of at least two medical images, each medical image highlighting at least one of the identified features by superimposing at least one of the masks on the obtained medical image, and displaying the set of at least two generated medical images, one after the other. The invention also relates to a microprocessor comprising a computer algorithm to perform the method of the invention and to a system comprising said microprocessor and a visualizing means.

16 Claims, 13 Drawing Sheets

(51) Int. Cl.
    *G06T 7/00*         (2017.01)
    *G06T 7/73*         (2017.01)
    *A61B 5/01*         (2006.01)
    *A61B 5/04*         (2006.01)
    *A61B 6/03*         (2006.01)
    *A61B 8/08*         (2006.01)
    *G06T 11/00*       (2006.01)
    *G06T 11/60*       (2006.01)
    *A61B 6/00*         (2006.01)
    *A61B 5/055*       (2006.01)
    *A61B 5/05*         (2006.01)

(52) U.S. Cl.
    CPC ........ *A61B 5/04008* (2013.01); *A61B 5/4244* (2013.01); *A61B 6/032* (2013.01); *A61B 6/037* (2013.01); *A61B 8/08* (2013.01); *G06T 7/0012* (2013.01); *G06T 7/73* (2017.01); *G06T 11/001* (2013.01); *G06T 11/60* (2013.01); *A61B 5/0059* (2013.01); *A61B 5/055* (2013.01); *A61B 5/0515* (2013.01); *A61B 5/0522* (2013.01); *A61B 6/463* (2013.01); *G06T 2207/10056* (2013.01); *G06T 2207/10072* (2013.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/30056* (2013.01); *G06T 2207/30096* (2013.01)

(58) Field of Classification Search
    CPC ......... A61B 6/037; A61B 8/08; G06T 7/0012; G06T 7/73; G06T 11/60; G06T 11/001; G06T 2207/30056; G06T 2207/30096
    USPC ........................................................ 382/128
See application file for complete search history.

(56) References Cited

U.S. PATENT DOCUMENTS

| | | |
|---|---|---|
| 2008/0260820 A1 | 10/2008 | Borrelly |
| 2011/0207134 A1 | 8/2011 | Faham |
| 2012/0010824 A1 | 1/2012 | Cales |
| 2012/0183188 A1* | 7/2012 | Moriya .................. G06F 19/321 |
| | | 382/128 |
| 2012/0226709 A1 | 9/2012 | Bhargava |
| 2014/0119668 A1* | 5/2014 | Kwon .................. G06T 11/005 |
| | | 382/232 |

FOREIGN PATENT DOCUMENTS

| | | |
|---|---|---|
| EP | 2772882 | 9/2014 |
| WO | 2007140814 | 12/2007 |
| WO | 2010058295 | 5/2010 |
| WO | 2011123068 | 10/2011 |

OTHER PUBLICATIONS

Duda et al. "Use of the Hough transformation to detect lines and curves in pictures" Comm ACM, 1972, 15(1):11-15.
Harris et al. "A combined corner and edge dectector" Proceedings of the 4th Alvey Vision Conference, 1988, 147-151.
Maniprasad et al. "Automatic registration and segmentation of pancreatic images" Proc. Intl. Soc. Mag. Reson. Med., 2007,15:2727.
International Search Report, dated Oct. 29, 2015, from corresponding PCT application.

* cited by examiner

METHOD FOR DISPLAYING MEDICAL IMAGES

FIELD OF INVENTION

The present invention relates to the analysis and reporting of images resulting from medical examination. In particular, the present invention relates to methods for displaying at least one easy-to-understand medical image highlighting features (such as lesions and morphometric data) in or from a medical image.

BACKGROUND OF INVENTION

Imaging is nowadays widely used in the medical field. Indeed, diagnostic methods may include recovering images from radiography, MRI, scanners, histology, etc. . . . , especially when the disease is characterized by the presence of lesions that can be visualized.

As every medical examination, medical examination involving recovering images results in a medical report, including general information (such as, for example, patient identification, patient gender and the like, date and location of the examination and the like) and specific medical information important for diagnosis. Specific medical information generally comprises two components: the first one is a descriptive analysis (corresponding to the description of what the physician sees on the medical image), while the second one is a diagnostic analysis (corresponding to the interpretation of the physician). The last part of the medical report is the conclusion, comprising a final diagnostic and possibly treatment options.

However, the medical report usually only includes text, and rarely comprises images. The major obstacle to the use of images in medical report is the complexity thereof: indeed, medical images may lack clarity for non-experts, who fail, for example, to visualize lesions with medical importance.

There is thus a need for a method for rendering a medical image easily understandable for non-experts (such as, for example, patients but also some physicians non-familiar with imaging), and allowing, for example, visualizing lesions on the medical image, and optionally rapidly assessing the severity thereof.

The present invention thus relates to a method for automatically highlighting lesions or morphometric data on a medical image, based on dynamic enhanced digitized images and image analysis. An example of a method of the invention is illustrated in FIG. 24. The method results in one or more easy-to-understand images, wherein each easy-to-understand image highlights one or more lesion or morphometric data identified on the medical digital image and optionally gives an information on the severity of said one or more lesion.

SUMMARY

The present invention relates to a method for displaying at least one easy-to-understand medical image, comprising the steps of:
a. obtaining a medical image,
b. identifying at least one feature on the image of step (a),
c. generating at least one mask highlighting the at least one feature,
d. displaying at least one easy-to-understand medical image including at least one mask, on which the at least one feature identified in step (b) is highlighted.

In one embodiment, the method of the invention is for displaying at least two easy-to-understand medical images, comprising the steps of:
a. obtaining at least one medical image,
b. identifying on the medical image of step a) at least two features,
c. generating masks showing the features of step b), each mask highlighting at least one feature identified in step b),
d. generating a set of at least two easy-to-understand medical images by superimposing at least one mask of step c) on the medical image of step a),
e. displaying the set of at least two easy-to-understand medical images of step d), one after the other, preferably in the form of a slide show or in any form where the images can be read sequentially, such as for example a film.

In one embodiment, the at least one medical image of step a) is a 2D image.

In one embodiment, the at least one easy-to-understand image is obtained by superimposing at least one mask of step (c) onto the medical image of step a), thereby producing at least one modified medical image on which the at least one feature identified in step (b) is highlighted.

In another embodiment, the at least one easy-to-understand image corresponds to one mask. In another embodiment, the at least one easy-to-understand image corresponds to the superimposition of at least two masks.

In one embodiment, the medical image is an image recovered by radiology, anatomy, pathology, histo-pathology, anatomo-pathology, cytology, nuclear medicine, endoscopy or biology. In one embodiment, the medical image is an image of whole or part of the liver of a subject, and/or wherein the at least one feature is a liver-related feature.

In one embodiment, the at least one feature is, or the at least two features are:
- a lesion, preferably selected from the group comprising whole fibrosis, bridging fibrosis, septa, porto-septal fibrosis, perisinusoidal fibrosis, portal fibrosis or stellar fibrosis, or
- a morphometric data, selected from the group comprising perimeter of an organ or fragment thereof and surface of an organ or fragment thereof.

In one embodiment, in step (b), an automated algorithm is used for identifying at least one feature in the medical image and/or for generating the mask. In one embodiment, in step (b), an automated algorithm is used for identifying at least one feature or the at least two features in the medical image. In another embodiment, in step (b), an automated algorithm is used for for generating the mask.

In one embodiment, the method comprises:
a) identifying a first feature on a medical image, generating a first mask corresponding to this feature and coloring the first mask in a first color,
b) optionally identifying a second feature on the medical image, generating a second mask corresponding to this feature and coloring the second mask in a second color which is preferably different from the first color,
c) optionally repeating step (b), preferably wherein every additional mask is colored in a different color, and
d) superimposing the at least one mask(s), optionally onto the medical image, thereby producing an easy-to-understand medical image highlighting the first, and optionally second and additional features identified in steps (a) to (c), wherein preferably each feature appears in a different color.

In one embodiment, the method comprises:
a) identifying a first feature on a medical image, generating a first mask corresponding to this feature and coloring the first mask in a first color,
b) identifying a second feature on the medical image, generating a second mask corresponding to this feature and coloring the second mask in a second color which is preferably different from the first color,
c) optionally repeating step (b), preferably wherein every additional mask is colored in a different color, and
d) superimposing the at least one mask(s), optionally onto the medical image, thereby producing an easy-to-understand medical image highlighting said features identified in steps (a) to (c), wherein preferably each feature appears in a different color.

In one embodiment, the method of the invention comprises:
a) identifying a first feature on a medical image, generating a first mask corresponding to this feature, coloring the first mask in a first color, and superimposing the first mask onto the medical image, thereby producing a first modified medical image highlighting the first feature,
b) identifying a second feature on the medical image, generating a second mask corresponding to this feature, coloring the second mask in a second color, and superimposing the second mask onto the first modified medical image obtained in step (a), thereby producing a second modified medical image highlighting the first and second feature,
c) optionally repeating step (b) and highlighting additional features, thereby producing a set of modified medical images.

In one embodiment, the method comprises:
a) identifying a first feature on a medical image, generating a first mask corresponding to this feature, and optionally superimposing the first mask onto the medical image, thereby producing a first easy-to-understand medical image highlighting the first feature, and
b) optionally repeating step (a), thereby producing additional easy-to-understand medical images, each highlighting one feature,
thereby producing a set of easy-to-understand medical image wherein each modified image highlights one feature.

In one embodiment, the color of the mask highlighting a feature reflects the abnormality level of a descriptor associated with said feature. In one embodiment, the color of the mask highlighting a lesion reflects the severity of said lesion.

In one embodiment, the at least one easy-to-understand image further comprises a legend or additional information.

In one embodiment, the method of the invention is computerized.

The present invention also relates to a microprocessor comprising a computer algorithm to perform the method as hereinabove described.

The present invention also relates to a system comprising:
a) a microprocessor as hereinabove described, and
b) a visualizing means to present the at least one modified medical images.

Definitions

In the present invention, the following terms have the following meanings:

In computer science, a mask may refer to a data that is used for bitwise operations, particularly in a bit field. Therefore, in the present invention, a "mask" refers to a black and white image of the same dimensions as the medical image (or of a region of interest thereof). As an example, on a mask of the invention, a specific feature may appear in black, while the rest of the image appear in white.

A "digital image" refers to a numeric representation (such as, for example, a binary representation) of a two-dimensional image.

An "analog image" refers to an image resulting from processing of a two-dimensional image conducted on two-dimensional analog signals by analog means.

"Lesions" refers to any abnormality in a tissue or an organ of an organism. In one embodiment of the invention, a lesion may be caused by a disease, and may consequently be referred as a "pathological lesion".

"Morphometric data" refers to a data relative to the quantitative analysis of a form, including the analysis of shape and size of a form.

The term "subject" refers to a mammal, preferably a human. In one embodiment, a subject may be a "patient", i.e. a warm-blooded animal, more preferably a human, who/which is awaiting the receipt of, or is receiving, medical care or was/is/will be the subject of a medical procedure, or is monitored for the development or progression of a disease.

DETAILED DESCRIPTION

The present invention relates to a method for displaying an easy-to-understand medical image, comprising the steps of:
a. obtaining a medical image,
b. identifying at least one feature on the image of step (a),
c. generating at least one mask highlighting the at least one feature,
d. displaying at least one easy-to-understand medical image including at least one mask, on which the at least one feature identified in step (b) is highlighted.

In one embodiment, the method of the invention is for displaying at least two easy-to-understand medical images, comprising the steps of:
a. obtaining at least one medical image,
b. identifying on the medical image of step a) at least two features,
c. generating masks showing the features of step b), each mask highlighting at least one feature identified in step b),
d. generating a set of at least two easy-to-understand medical images by superimposing at least one mask of step c) on the medical image of step a),
e. displaying the set of at least two easy-to-understand medical images of step d), one after the other, in the form of a slide show.

In one embodiment, the method of the invention is for rendering a medical image easy-to-understand for a person which is not a medical expert, such as, for example, for a patient. Therefore, in one embodiment, the method of the invention is not a diagnostic method.

In one embodiment, the method of the invention is for displaying at least one (preferably 1, 2, 3, 4, 5, 6, 7, 8, 9, 10 or more) easy-to-understand image.

In another embodiment, the method of the invention is for displaying a set of easy-to-understand images in the form of a slide show, wherein each image is displayed one after the other, preferably in a predetermined order and optionally with a predetermined period of time between each image display.

Therefore, in one embodiment, the method of the invention comprises displaying in a predefined order a set of images, wherein each image highlights a specific feature, or wherein each image highlights an additional feature as compared to the previous image of the slide show. The sequential display of features thus allows the image to be easy-to-understand, even for a person which is not an expert of the medical field.

In one embodiment, the at least one easy-to-understand medical image is obtained by superimposing the at least one mask onto the medical image, thereby producing at least one modified medical image on which the at least one feature identified in step (b) is highlighted. In this embodiment, the easy-to-understand image may be referred as a "modified image".

In another embodiment, the at least one easy-to-understand image is a mask generated in step (c).

In another embodiment, the at least one easy-to-understand image is obtained by superimposing at least two masks generated in step (c).

In one embodiment, the medical image is a 2D or 3D image, preferably a 2D image.

In one embodiment, the medical image is an image recovered by a medical imagery procedure from a subject, wherein the subject is a mammal, preferably a human, more preferably a patient.

Examples of medical imaging procedures that may be used for recovering the medical image of the invention include, but are not limited to, radiology, anatomy, pathology, histo-pathology, anatomo-pathology, cytology, nuclear medicine, endoscopy and biology. Preferably, the medical imaging procedure is histo-pathology or radiography.

In a first embodiment, the medical image is recovered directly after the medical examination. In a second embodiment, the medical image is a scanned image of the medical examination result.

In one embodiment, the medical image of step a) is analogic. In another embodiment, the medical image of step a) is digital.

In one embodiment, the at least one easy-to-understand image is analogic. In one embodiment, the at least one easy-to-understand image is digital.

In one embodiment of the invention, the medical image is an image from a tissue sample taken by biopsy or any other procedure such as, for example, surgery resection, such as, for example, an image of a histological section of a biopsy. As used herein, the term "histological section" refers to a thin slice of tissue applied to a microscopic slide. In one embodiment, the histological section was stained before obtaining an image thereof. Types of staining applied on the histological section may depend on the tissue or organ and on the lesion to be detected.

In one embodiment of the invention, the biopsy sample is a liver biopsy sample, and the histological section of said liver biopsy sample was stained with picro-sirius red. This staining highlights the fibrosis in red, healthy tissues in yellow/orange whereas steatosis remains in white (i.e. optically empty).

In one embodiment of the invention, the histological section is then scanned in order to obtain a medical image that will be analyzed in the method of the invention. A non-limiting example of scan parameters is by using an Aperio digital slide scanner (Scanscope CS System, Aperio Technologies, USA) image processor that provides high quality 30 000×30 000 pixel images at a resolution of 0.5 μm/pixel (magnification ×20).

In another embodiment of the invention, the histological section is observed by an optical technique. Examples of optical techniques include, but are not limited to microscopic physical imaging, such as, for example electron microscopy, second harmonic generation (SHG), multiphoton imaging, coherent anti-Stokes Raman scattering—CARS), two-photon excitation fluorescence (TPEF), diffuse optical imaging or event-related optical signal, and the resulting image is then recovered to be analyzed in the method of the present invention.

In another embodiment, the medical image is recovered by a non-optical technique. Examples of non-optical techniques include, but are not limited to, radiography (such as, for example, X-ray, ultrasonography, tomodensitometry (TDM), computerized scanner (CT-scan), magnetic resonance imaging (MRI), functional magnetic resonance imaging (fMRI), tomography, computed axial tomography, proton emission tomography (PET) or single photon emission computed tomography (SPECT)); nuclear medicine (such as, for example, scintigraphy); photoacoustic methods; thermal methods; and magneto-encephalography.

In one embodiment, the medical image is an image recovered for analyzing the status or the functionality of the liver of a subject (such as, for example, for assessing the presence or severity of fibrosis in the liver of a subject). According to this embodiment, the medical image preferably is an image of whole or part of the liver of the subject. According to this embodiment, the medical image may be a scanned image of a liver biopsy sample, or a image resulting from liver CT-scan.

In one embodiment, the medical image is pre-treated before implementing the method of the invention.

Examples of pre-treatment include, but are not limited to, compression, transformation of the medical image in a binary image, such as, for example, a black and white image (using automated thresholding for example); removal of artefacts and the like.

The skilled artisan is a specialist of image analysis of organs and tissues, and knows what artefacts should be removed before analysis of the medical image. Examples of artefacts that may be removed from the medical image include, but are not limited to folds, dust, and optionally large blood vessels, large biliary tracts and the like. In one embodiment, pre-treatment of the medical image comprises elimination of very small areas, considered as noise, elimination of vessels surrounding fibrosis, elimination of non-round regions, such as, for example, biliary tracts, or elimination of heterogeneous regions, such as, for example, blood vessels.

In one embodiment, pre-treatment of the medical image comprises detecting the white background of the medical image so that it is not taken into account in the analysis.

In one embodiment of the invention, in order to facilitate sharing and storage thereof, the medical image may be compressed, such as, for example, using a JPEG2000 software.

In one embodiment, the method of the invention comprises defining a region of interest on the medical image. Said definition may require a manual input or the use of a pattern recognition algorithm.

In one embodiment, the medical image is an image of whole or part of the liver of a subject, and the feature is thus a "liver-related" feature, i.e. identified on an image of the liver or of part thereof. Examples of liver-related features include, but are not limited to, edges of a liver biopsy, Arantius furrow surface or perimeter, liver perimeter or surface, surface or perimeter of liver segment I, surface or perimeter of liver segment IV fibrosis, steatosis, liver fibrosis, cirrhosis, liver steatosis, fragmentation, or non-alcoholic steato-hepatitis (NASH).

In one embodiment, the at least one feature identified on the medical image is/are lesions, such as, for example, fibrosis, steatosis, fragmentation of an organ or fragment thereof, lesions induced by inflammation, tumors, polyps, nodules, cyst, ulcers, and the like. In one embodiment, the lesion is not steatosis.

In one embodiment, the lesion is a tissue lesion, either parenchymal or extraparenchymal. In one embodiment, the lesion is not a tumor. In another embodiment, the lesion is not associated with a blood vessel, preferably is not associated with a large blood vessel.

In one embodiment, the medical image is an image of whole or part of the liver of a subject, and the lesion is preferably related to a liver disease.

Examples of liver lesions include, but are not limited to, liver fibrosis, cirrhosis, liver steatosis, fragmentation, or non-alcoholic steato-hepatitis (NASH). Preferably, said liver lesion is liver fibrosis.

Examples of liver diseases include, but are not limited to, acute liver diseases and chronic liver diseases. Specific examples of liver diseases that may cause lesions to the liver include, but are not limited to chronic viral hepatitis C, chronic viral hepatitis B, chronic viral hepatitis D, chronic viral hepatitis E, non-alcoholic fatty liver disease (NAFLD), alcoholic chronic liver disease, autoimmune hepatitis, hemochromatosis, Wilson disease and acquired or inherited metabolic disorders.

According to an embodiment, the subject, including a human, is at risk of presenting a lesion in an organ or a tissue; or presents a lesion in an organ or a tissue. In one embodiment, said risk may correspond to a family predisposition to lesions, to a genetic predisposition to lesions, or to an environmental exposure to compounds and/or to conditions promoting the appearance or development of lesions.

Fibrosis can start in the centro-lobular region (alcoholic liver disease) and/or in the periphery of the liver lobule or around the portal tracts (viral liver disease). This fibrosis grows gradually to form bands of fibrosis, or septa, called septal fibrosis. Septal fibrosis is extended between the portal tracts or between the portal tracts and the centro-lobular region. The cirrhosis stage occurs when these different septa entirely surround hepatocytes. When pathologists are assessing the Metavir stage (reflecting the severity of fibrosis), their judgment is based on the porto-septal fibrosis. Another form of fibrosis is located between the rows of hepatocytes and sinusoids (the equivalent of the capillary in the liver), i.e. in the intercellular space where there are many liver metabolic exchanges. This form of fibrosis is called peri-sinusoidal fibrosis. Although it is usually not taken into account in the fibrosis scores in clinical use, peri-sinusoidal fibrosis is important because it has a key role in the genesis of liver failure and portal hypertension. Moreover, bridging fibrosis (also referred herein as "bridges") is a characteristic of F3 Metavir stage (severe fibrosis).

Therefore, the method of the invention may comprise highlighting total fibrosis and/or components thereof, i.e. porto-septal fibrosis or components thereof and peri-sinusoidal fibrosis. Components of porto-septal fibrosis include portal fibrosis (including bridging fibrosis and simple septa) and stellar fibrosis.

In one embodiment, the method of the invention comprises highlighting a lesion that does not comprise fibrosis but that is secondary or related to fibrosis, such as, for example, parenchymal nodules, specimen fragmentation, irregular edges . . . .

In another embodiment of the invention, the lesion is steatosis.

In one embodiment of the invention, steatosis is liver steatosis, and is related to FLD (Fatty Liver Disease). FLD encompasses a wide range of potentially reversible conditions involving the liver, wherein large vacuoles of triglycerides fat accumulate in hepatocytes via the process of steatosis (i.e. the abnormal retention of lipids within a cell). FLD is commonly associated with alcohol or metabolic disorders (such as, for example, diabetes, hypertension, dyslipidemia, abetalipoproteinemia, glycogen storage diseases, Weber-Christian disease, Wolman disease, acute fatty liver of pregnancy or lipodystrophy). However, it can also be due to nutritional causes (such as, for example, malnutrition, total parenteral nutrition, severe weight loss, refeeding syndrome, jejuno-ileal bypass, gastric bypass or jejunal diverticulosis with bacterial overgrowth), as well as to consumption of various drugs and toxins (such as, for example, amiodarone, methotrexate, diltiazem, highly active antiretroviral therapy, glucocorticoids, tamoxifen or environmental hepatotoxins) and to other diseases such as inflammatory bowel disease or HIV.

Whether it is AFLD (Alcoholic Fatty Liver Disease) or NAFLD (Non-Alcoholic Fatty Liver Disease), FLD encompasses a morphological spectrum consisting from the mildest type "liver steatosis" (fatty liver), called NAFL, to the potentially more serious type "steatohepatitis", called NASH, which is associated with liver-damaging inflammation and, sometimes, the formation of fibrous tissue. In fact, steatohepatitis has the inherent propensity to progress towards the development of fibrosis then cirrhosis which can produce progressive, irreversible liver scarring or towards hepatocellular carcinoma (liver cancer). Therefore, in one embodiment, steatosis is simple liver steatosis or NAFL (Non-alcoholic fatty liver). In another embodiment, steatosis is part of steatohepatitis or NASH.

In another embodiment of the invention, the lesion is inflammation. In one embodiment where the organ is liver, inflammation may refer to NASH.

In one embodiment, the at least one feature(s) identified on the medical image is/are morphometric data, such as, for example, surface of an organ or fragment thereof, perimeter of an organ or fragment thereof, edges of the image or of an organ or fragment thereof.

In one embodiment where the medical image is an image of whole or part of the liver of a subject, one or more of the non-limitative following morphometric data may be identified: edges of a liver biopsy, Arantius furrow surface or perimeter, liver perimeter or surface, spleen perimeter or surface, surface or perimeter of liver segment I, surface or perimeter of liver segment IV and the like.

According to one embodiment of the invention, the identification of features on the medical image of step a) is performed using an automated algorithm. Examples of automated algorithms that may be used are well-known from the skilled artisan. An example of automated algorithm that may be used in the present invention is the one described in the European patent application EP 13 157 488.1 which is incorporated herein by reference.

In one embodiment, the method of the invention comprises identifying and highlighting 1, 2, 3, 4, 5, 6, 7, 8, 9, 10 or more features on the medical image.

In one embodiment, the method of the invention comprises identifying and highlighting total fibrosis.

In another embodiment, the method of the invention comprises identifying and highlighting porto-septal fibrosis.

In another embodiment, the method of the invention comprises identifying and highlighting peri-sinusoidal fibrosis and porto-septal fibrosis.

In another embodiment, the method of the invention comprises identifying and highlighting peri-sinusoidal fibrosis, portal fibrosis and stellar fibrosis.

In another embodiment, the method of the invention comprises identifying and highlighting peri-sinusoidal fibrosis, simple septa, stellar fibrosis and edges of a liver biopsy.

In another embodiment, the method of the invention comprises identifying and highlighting Arantius furrow.

In another embodiment, the method of the invention comprises identifying and highlighting liver perimeter.

In another embodiment, the method of the invention comprises identifying and highlighting spleen perimeter.

In another embodiment, the method of the invention comprises identifying and highlighting spleen surface and liver surface.

In another embodiment, the method of the invention comprises identifying and highlighting liver segment I surface.

In one embodiment, a mask of the invention highlights at least one feature identified in step (b), preferably one or two features identified in step (b). As used herein, a mask highlighting a feature may be referred as a "mask corresponding to" said feature.

As used herein, the expression "a mask highlights a feature" means that on this mask, the feature (such as, for example, the surface or the contour of the feature) may appear in a first color, for example black, while the rest of the image appears in a color contrasting or complementary to the first color, for example white. Examples of masks are shown in the Examples.

Examples of masks that may be generated in the method of the invention include, but are not limited to:
  total fibrosis mask, wherein total fibrosis appears in black while the rest of the image is in white. This mask may be for example generated from a histological image from a liver biopsy. An example of this mask is shown in FIG. 13,
  porto-septal fibrosis mask, wherein porto-septal fibrosis appears in black while the rest of the image is in white. This mask may be for example generated from a histological image from a liver biopsy. An example of this mask is shown in FIG. 14,
  perisinusoidal fibrosis mask, wherein perisinusoidal fibrosis appears in black while the rest of the image is in white. This mask may be for example generated from a histological image from a liver biopsy. An example of this mask is shown in FIG. 15,
  portal fibrosis mask, wherein portal fibrosis appears in black while the rest of the image is in white. This mask may be for example generated from a histological image from a liver biopsy,
  stellar fibrosis mask, wherein stellar fibrosis appears in black while the rest of the image is in white. This mask may be for example generated from a histological image from a liver biopsy. An example of this mask is shown in FIG. 16,
  bridging fibrosis mask, wherein bridging fibrosis appears in black while the rest of the image is in white. This mask may be for example generated from a histological image from a liver biopsy. An example of this mask is shown in FIG. 17,
  simple septa mask, wherein simple septa appear in black while the rest of the image is in white. This mask may be for example generated from a histological image from a liver biopsy,
  biopsy edge mask, wherein the edges of a biopsy appear in black while the rest of the image is in white: this mask may only be generated from an image of a biopsy, such as, for example, a liver biopsy. An example of this mask is shown in FIG. 18,
  biopsy specimen surface mask, wherein the surface of a biopsy specimen appears in black while the rest of the image is in white: this mask may only be generated from an image of a biopsy, such as, for example, a liver biopsy,
  Arantius furrow perimeter mask, wherein the contour of Arantius furrow appears in black while the rest of the image is in white. This mask may be generated from an image wherein the whole liver may be visualized, such as a liver CT-scan image,
  Arantius furrow surface mask, wherein the surface of Arantius furrow appears in black while the rest of the image is in white. This mask may be generated from an image wherein the whole liver may be visualized, such as a liver CT-scan image,
  liver perimeter mask, wherein the contour of the liver appears in black while the rest of the image is in white. This mask may be generated from an image wherein the whole liver may be visualized, such as a liver CT-scan image,
  liver surface mask, wherein the surface of the liver appears in black while the rest of the image is in white. This mask may be generated from an image wherein the whole liver may be visualized, such as a liver CT-scan image,
  spleen perimeter mask, wherein the contour of the spleen appears in black while the rest of the image is in white. This mask may be generated from an image wherein the whole spleen may be visualized, such as a liver CT-scan image,
  spleen surface and liver surface mask, wherein the surface of the spleen appears in black while the rest of the image is in white. This mask may be generated from an image wherein the whole spleen may be visualized, such as a liver CT-scan image,
  liver segment I perimeter mask, wherein the contour of the liver segment I appears in black while the rest of the image is in white. This mask may be generated from an image wherein the whole liver may be visualized, such as a liver CT-scan image,
  liver segment I surface mask, wherein the surface of the liver segment I appears in black while the rest of the image is in white. This mask may be generated from an image wherein the whole liver may be visualized, such as a liver CT-scan image,
  liver segment IV perimeter mask, wherein the contour of the liver segment IV appears in black while the rest of the image is in white. This mask may be generated from an image wherein the whole liver may be visualized, such as a liver CT-scan image,
  liver segment IV surface mask, wherein the surface of the liver segment IV appears in black while the rest of the image is in white. This mask may be generated from an image wherein the whole liver may be visualized, such as a liver CT-scan image,
  liver and spleen surfaces mask, wherein the surface of the liver and the surface of the spleen appear in black while the rest of the image is in white. This mask may be generated from an image wherein the whole liver and spleen may be visualized, such as a liver CT-scan image, and liver and spleen perimeters mask, wherein the contour of the liver and the contour of the spleen appear in black while the rest of the image is in white. This mask may be generated from an image wherein the whole liver and spleen may be visualized, such as a liver CT-scan image.

In one embodiment, the method may further comprise measuring descriptors on the image. As used herein, a descriptor refers to any computer-generated data (preferably any figure) associated with or derived from a medical image of an organ or tissue or fragment thereof.

Examples of descriptors include the descriptors described in the European patent application EP 13 157 488.1 which is incorporated herein by reference. These descriptors include, but are not limited to: fractal dimension of the edges of the organ or fragment thereof, linearity percentage of the edges, nodularity of the curved and irregular edges of the organ or fragment thereof, angularity, length of the organ or fragment thereof, height of the organ or fragment thereof, perimeter of the organ or fragment thereof, mean and total native perimeter of the organ or fragment thereof, smoothed perimeter of the organ or fragment thereof, ratio between the native and smoothed perimeters, also referred as anfractuosity, largest perimeter of the organ or fragment thereof, indentation of the organ or fragment thereof, area of the organ or fragment thereof, granularity percentage, fragmentation, mean intensity of the image on the red, blue or green component, luminosity of fibrosis staining in the red, green and/or blue components, luminosity of the parenchyma staining in the red, green and/or blue components, organ fat ratio, abdominal fat ratio, hypertrophy of liver segment I, surface of the segment I, width of the liver segment IV, sagittal or frontal length of liver segment I or IV, ratio between segment I and segment IV dimensions, furrow thickness, surface of the furrow, internal nodularity in the liver, diameter of the portal vein, heterogeneity of the density intensity, fractal organization of the organ, mean total density of the image, standard deviation of total density of the image, coefficient of variation of total density of the image, median total density of the image, interquartile range of total density of the image, ratio between interquartile range of total density and median of total density of the image, mean surface of the organ or fragment thereof, total surface of the organ or fragment thereof, total mean surface of the organ or fragment thereof, ratio between the organ (or fragment thereof) perimeter and the organ (or fragment thereof) surface, ratio between spleen surface and liver surface, ratio between spleen perimeter and liver perimeter, ratio between segment I surface and liver surface, Arantius furrow thickness, Arantius furrow surface, portal furrow thickness, area of fibrosis, fractal dimension of fibrosis, nodularity percentage, number of nodules, number of nodules with more than 30% of fibrosis around, area of steatosis, relative area of steatosis, fractal dimension of steatosis, area of porto-septal fibrosis, fractal dimension of porto-septal fibrosis, area of peri-sinusoidal fibrosis, fractal dimension of peri-sinusoidal fibrosis, area of lobular peri-sinusoidal fibrosis, ratio of peri-sinusoidal fibrosis area, luminosity contrast between fibrosis and parenchyma, luminosity contrast between fibrosis and the organ or fragment thereof, whole area of stellar fibrosis, portal area of stellar fibrosis, lobular area of stellar fibrosis, number of porto-septal regions; mean area of stellar fibrosis, mean area of porto-septal regions, number of bridges, portal ratio of bridges, area of fibrosis in the bridges, bridges thickness, bridges perimeter, bridge area, portal distance, and number of fragments.

In one embodiment, descriptors associated with the quality of the medical image may be measured. Examples of descriptors associated with the quality of the medical image include, but are not limited to, density heterogeneity, mean intensity of the image on the red, blue or green component, luminosity of fibrosis staining in the red, green and/or blue components, luminosity of the parenchyma staining in the red, green and/or blue components, luminosity contrast between fibrosis and parenchyma, luminosity contrast between fibrosis and the organ or fragment thereof. Preferably, the method of the invention comprises measuring density heterogeneity of the medical image.

In one embodiment, a descriptor on the image is associated with a specific lesion, and the value of the descriptor may be indicative of the severity of said lesion.

In one embodiment, descriptors associated with a feature are measured. Non-limitative examples of descriptors associated with a feature are shown below:

when the feature is total fibrosis, examples of descriptors that may be measured include, but are not limited to, fractal dimension of fibrosis, area of fibrosis, and number of nodules with more than 30% of fibrosis around, when the feature is porto-septal fibrosis, examples of descriptors that may be measured include, but are not limited to, area of porto-septal fibrosis, fractal dimension of porto-septal fibrosis, number of porto-septal regions; and mean area of porto-septal regions, when the feature is peri-sinusoidal fibrosis, examples of descriptors that may be measured include, but are not limited to, area of peri-sinusoidal fibrosis, fractal dimension of peri-sinusoidal fibrosis, area of lobular peri-sinusoidal fibrosis and ratio of peri-sinusoidal fibrosis area vs another descriptor, when the feature is portal fibrosis, examples of descriptors that may be measured include, but are not limited to, portal distance such as, for example, mean distance between portal spaces, and portal fibrosis area, when the feature is stellar fibrosis, examples of descriptors that may be measured include, but are not limited to, whole area of stellar fibrosis, portal area of stellar fibrosis, lobular area of stellar fibrosis, and mean area of stellar fibrosis, when the feature is bridging fibrosis or bridges, examples of descriptors that may be measured include, but are not limited to, number of bridges, portal ratio of bridges, area of fibrosis in the bridges, bridges thickness, bridges perimeter, and bridge area, when the feature is simple septa, examples of descriptors that may be measured include, but are not limited to number of bridges, and bridge thickness, when the feature is steatosis, examples of descriptors that may be measured include, but are not limited to, area of steatosis (wherein the reference is whole liver), relative area of steatosis (wherein the reference is non-fibrotic liver), fractal dimension of steatosis, organ fat ratio, and abdominal fat ratio vs another descriptor, when the feature is the edges (of a biopsy or of an organ or fragment thereof), examples of descriptors that may be measured include, but are not limited to, fractal dimension of the edges, linearity percentage of the edges, nodularity of the curved and irregular edges of the organ or of a fragment thereof, angularity, length of the organ or fragment thereof, height of the organ or fragment thereof, perimeter of the organ or fragment thereof, mean and total native perimeter of the organ, smoothed perimeter of the organ or fragment thereof, ratio between the native and smoothed perimeters, also referred as anfractuosity, largest perimeter of the organ or fragment thereof, indentation of the organ or fragment thereof, area of the organ or fragment thereof, when the feature is Arantius furrow perimeter, examples of descriptors that may be measured include, but are not limited to, Arantius furrow thickness and Arantius furrow surface, when the feature is Arantius furrow surface, examples of descriptors that may be measured include, but are not limited to, Arantius furrow thickness and Arantius furrow surface, when the feature is liver perimeter, examples of descriptors that may be measured include, but are not limited to, length of the liver, height of the liver, liver perimeter, mean and total native liver perimeter, smoothed liver perimeter, ratio between the native and smoothed liver perimeters, also referred as anfractuosity, largest perimeter of the liver, indentation of the liver, ratio between the liver perimeter and the liver surface, and area of the liver, when the feature is liver surface, examples of descriptors that may be measured include, but are not limited to, length of the liver, height of the liver, liver perimeter, mean and total native liver perimeter, smoothed liver perimeter, ratio between the native and smoothed liver perimeters, also referred as anfractuosity, largest perimeter of the liver, indentation of the liver, ratio between the liver perimeter and the liver surface, and area of the liver, when the feature is spleen perimeter, examples of descriptors that may be measured include, but are not limited to, length of the spleen, height of the spleen, spleen perimeter, mean and total native spleen perimeter, smoothed spleen perimeter, ratio between the native and smoothed spleen perimeters, also referred as anfractuosity, largest perimeter of the spleen, indentation of the spleen, ratio between the spleen perimeter and the spleen surface, and area of the spleen, when the feature is spleen surface and liver surface, examples of descriptors that may be measured include, but are not limited to, length of the spleen, height of the spleen, spleen perimeter, mean and total native spleen perimeter, smoothed spleen perimeter, ratio between the native and smoothed spleen perimeters, also referred as anfractuosity, largest perimeter of the spleen, indentation of the spleen, ratio between the spleen perimeter and the spleen surface, and area of the spleen, when the feature is liver segment I perimeter, examples of descriptors that may be measured include, but are not limited to, length (such as, for example, frontal or sagittal length) of the liver segment I, height of the liver segment I, liver segment I perimeter, mean and total native liver segment I perimeter, smoothed liver segment I perimeter, ratio between the native and smoothed liver segment I perimeters, also referred as anfractuosity, largest perimeter of the liver segment I, indentation of the liver segment I, area of the liver segment I, hypertrophy of liver segment I, surface of the segment I, ratio between segment I and segment IV dimensions, ratio between the liver segment I perimeter and the liver segment I surface, and ratio between segment I surface and liver surface, when the feature is liver segment I surface, examples of descriptors that may be measured include, but are not limited to, length (such as, for example, frontal or sagittal length) of the liver segment I, height of the liver segment I, liver segment I perimeter, mean and total native liver segment I perimeter, smoothed liver segment I perimeter, ratio between the native and smoothed liver segment I perimeters, also referred as anfractuosity, largest perimeter of the liver segment I, indentation of the liver segment I, area of the liver segment I, hypertrophy of liver segment I, surface of the segment I, ratio between segment I and segment IV dimensions, ratio between the liver segment I perimeter and the liver segment I surface, and ratio between segment I surface and liver surface, when the feature is liver segment IV perimeter, examples of descriptors that may be measured include, but are not limited to, length (such as, for example, frontal or sagittal length) of the liver segment IV, height of the liver segment IV, liver segment IV perimeter, mean and total native liver segment IV perimeter, smoothed liver segment IV perimeter, ratio between the native and smoothed liver segment IV perimeters, also referred as anfractuosity, largest perimeter of the liver segment IV, indentation of the liver segment IV, area of the liver segment IV, width of the liver segment IV, ratio between the liver segment IV perimeter and the liver segment IV surface, and ratio between segment I and segment IV dimensions, when the feature is liver segment IV surface, examples of descriptors that may be measured include, but are not limited to, length (such as, for example, frontal or sagittal length) of the liver segment IV, height of the liver segment IV, liver segment IV perimeter, mean and total native liver segment IV perimeter, smoothed liver segment IV perimeter, ratio between the native and smoothed liver segment IV perimeters, also referred as anfractuosity, largest perimeter of the liver segment IV, indentation of the liver segment IV, area of the liver segment IV, width of the liver segment IV, ratio between the liver segment IV perimeter and the liver segment IV surface, and ratio between segment I and segment IV dimensions, when the features are liver and spleen surfaces mask, examples of descriptors that may be measured include, but are not limited to, ratio between spleen surface and liver surface and ratio between spleen perimeter and liver perimeter, when the feature is liver and spleen perimeters, examples of descriptors that may be measured include, but are not limited to, ratio between spleen surface and liver surface and ratio between spleen perimeter and liver perimeter.

In one embodiment, at least one of the following descriptors may be measured in the method of the invention: fractal dimension of porto-septal fibrosis, fractal dimension of peri-sinusoidal fibrosis, ratio of peri-sinusoidal fibrosis area, whole area of stellar fibrosis, portal area of stellar fibrosis, mean portal distance, number of bridges, portal ratio of the bridges, mean bridge thickness, mean granularity percentage, mean nodularity percentage, fragmentation index, edge linearity percentage, density heterogeneity, Arantius furrow width, mean liver perimeter, mean spleen perimeter, ratio of spleen to liver surface, frontal (transversal) or sagittal (antero-posterior) length of liver segment I, and whole spleen perimeter.

Preferably, the descriptors are measured according to the automated morphometric method described in EP 13 157 488.1 which is incorporated herein by reference.

Examples of methods that may be used for measuring descriptors are presented below.

In one embodiment, fractal dimension of porto-septal fibrosis may be measured using the "box-counting" method (Moal et al, Hepatology, 2002, 36:840-849). The box-counting method provides the fractal dimension of Kolmogorov (D). The technique has been reported in details for biological structures. Briefly, a grid of square boxes (with $\epsilon$ pixels as the side length) resembling a chessboard is superimposed over the mask corresponding to porto-septal fibrosis. Boxes intersecting with collagen fibers are counted. Another chessboard grid is then used to cover the entire surface of the medical image. Thus, the total number (N) of boxes of sides ($\epsilon$) required to completely cover the collagen fibers reflects the perimeter examined with the scale ratio $\epsilon$. In one embodiment, this step is repeated with $\epsilon$ varying until a size of about 14 pixels, and data are plotted on a log-log graph (i.e., log [N] against log [$\epsilon$]). The relationship between points is measured by linear regression analysis using the least square method; the slope D of the regression line corresponds to the fractal dimension of porto-septal fibrosis.

In one embodiment, fractal dimension of peri-sinusoidal fibrosis may be measured according to the method described hereinabove for measuring the fractal dimension of porto-septal fibrosis using the mask corresponding to peri-sinusoidal fibrosis.

In one embodiment, the ratio of peri-sinusoidal fibrosis area corresponds to the ratio of peri-sinusoidal fibrosis among the whole fibrosis of the medical image, and may be calculated as follows:

ratio of peri-sinusoidal fibrosis area=$Pix_{FPS}/Pix_{FIB\_TOT}*100$ wherein $Pix_{FPS}$ is the number of pixels of the mask corresponding to peri-sinusoidal fibrosis and $Pix_{FIB\_TOT}$ is the number of pixels of the mask corresponding to total fibrosis.

In one embodiment, the whole area of stellar fibrosis corresponds to the ratio between area of stellar fibrosis among the total surface of a liver biopsy specimen, may be calculated as follows:

whole area of stellar fibrosis=Pix_Fib_Stellar/PixMASK_LB*100 wherein Pix_Fib_Stellar is the number of pixels of the mask corresponding to stellar fibrosis, and PixMASK_LB is the number of pixels of the mask corresponding to the surface of the liver biopsy specimen.

In one embodiment, portal area of stellar fibrosis corresponds to the area of stellar fibrosis among the surface of porto-septal regions, and may be calculated as follows:

portal area of stellar fibrosis=Pix_Fib_Stellar/Pix_Mask_Port*100, wherein Pix_Fib_Stellar is the number of pixels of the mask corresponding to stellar fibrosis and Pix_Mask_Port is the number of pixels of the mask corresponding to porto-septal fibrosis.

In one embodiment, mean portal distance is a descriptor corresponding to the mean distance between porto-septal regions for all fragments. It may be calculated as follows:

mean portal distance=$(Dmoy_{1}+Dmoy_{2}+\ldots Dmoy_{NB\_FRAG})/NB\_FRAG$ wherein NB_FRAG is the number of fragments in the mask corresponding to the surface of the liver biopsy specimen and $Dmoy_n=Dmin_n/(Nb\_EPn-1)$ (wherein for each fragment n, the minimum distance $Dmin_n$ between all porto-septal regions present on the mask corresponding to porto-septal fibrosis is measured).

In one embodiment, the number of bridges corresponds to the number of bridges in the mask corresponding to bridging fibrosis.

In one embodiment, the portal ratio of the bridges corresponds to the ratio of bridges among the porto-septal areas, and may be measured as follows:

portal ratio of the bridges=Pix_Mask_Bridge/Pix_Mask_Port*100 wherein Pix_Mask_Bridge is the number of pixels in the mask corresponding to bridging fibrosis, and Pix_Mask_Port is the number of pixels of the mask corresponding to porto-septal fibrosis.

In one embodiment, the mean bridge thickness is a descriptor resulting from the following ratio:

mean bridge thickness=MEAN_SURF_BRIDGE/MEAN_PERIM_BRIDGE*100 wherein MEAN_SURF_BRIDGE is the mean of pixels representing the surface of bridges and MEAN_PERIM_BRIDGE is the mean of pixels representing the perimeter of bridges, which are both measured on the mask corresponding to bridging fibrosis.

In one embodiment, the descriptor "mean granularity percentage" is measured. The measure of the mean granularity percentage aims at quantifying the impairment of the structure (i.e. destructuration) of an organ or tissue due to the presence of a lesion. Mean granularity percentage is the ratio between the number of fragments without destructuration and the number of granules obtained in these fragments after destructuration by porto-septal areas:

mean granularity percentage=100−(NB_FRAG/Nb_Granules*100)

wherein NB_FRAG is the number of fragments in the mask corresponding to the surface of the liver biopsy specimen and Nb_Granules is the number of granules obtained in these fragments.

In one embodiment, mean nodularity percentage is measured. Nodules are the result of the disruption of fibrosis that circles regions of tissue (parenchyma), that may be defined as circular and non-fibrotic (without fibrous septa inside) area surrounded by fibrosis. Nodularity percentage corresponds to the mean percentage of fibrosis around areas. In one embodiment, the measure of the mean nodularity percentage is carried out the same way as the mean granularity percentage (see hereinabove), wherein only circular granules are kept.

In one embodiment, the descriptor "fragmentation index" is measured. Indeed, depending on the METAVIR stage, a liver biopsy specimen may be fragmented. In particular, for the F4 stage, the liver biopsy specimen could contain several small fragments. Therefore, the measure of the fragmentation index can be useful for the high fibrosis stages with a little mean granularity percentage because of a numerous fragmentation. For measuring the fragmentation index, small fragments are detected on the mask corresponding to the surface of the liver biopsy specimen. In one embodiment, a small fragment has a surface under 2 mm$^2$ or a surface under 3 mm$^2$ but with a circularity up to 0.7. The fragmentation index is the ratio between the surface of small fragments detected and the total surface of the liver biopsy specimen.

In one embodiment, edge linearity percentage is measured. The analysis of the edges of an organ or of a fragment thereof (for example a biopsy specimen) is an important descriptor for assessing the presence and/or the severity of a lesion or for diagnosing a disease of for a prognosis. In one embodiment, the Hough transform is applied to detect straight lines on the mask corresponding to the edge (Duda et al, Comm ACM, 1972, 15:11-15), leading to a mask containing only the edges of the mask detected as straight by the Hough transform ("hough mask"). In parallel, a straight mask ("rect mask") is created from the mask corresponding to the edge, using a Harris detector (Harris et al, Proceedings of the 4$^{th}$ Alvey Vision Conference, 1988:147-151). Therefore, rect mask represents the edges of mask corresponding to the edge that are in common with this theoretical straight mask. Then, a third mask is obtained by the combination of both previous masks ("combination mask") thus containing all the straightest edges of the organ, tissue or fragment thereof. The mean linearity percentage may be calculated as follows:

$$\text{mean linearity percentage} = \text{Pix}_{MaskRectComb} / \text{Pix}_{MaskEdge} * 100$$

wherein $\text{Pix}_{MaskRectComb}$ is the number of pixels of the combination mask and $\text{Pix}_{MaskEdge}$ is the number of pixels of the mask corresponding to the edge.

In one embodiment, the method of the invention comprises measuring density heterogeneity, corresponding to the heterogeneity of the density intensity in the medical image between several regions of interest. This descriptor may be measured for example from the mask corresponding to the surface of a liver biopsy specimen.

In one embodiment, a mask generated in step (c) of the method of the invention may be colored, i.e. the feature originally in a first color, for example black, on the mask is colored in a different color from the first color (and preferably not in black or in white).

In one embodiment, all masks generated in step (c) of the method of the invention are colored, preferably using different colors so that each single feature identified in the medical image is colored in a different color.

In one embodiment, the color or the intensity of the color applied to a mask corresponding to a feature depends on the abnormality of a descriptor associated with said feature. Therefore, in one embodiment, the color or the intensity of the color applied to a mask corresponding to a lesion depends on the severity of the lesion. Therefore, according to this embodiment, the color or the intensity of the color of the mask corresponding to a feature (in particular a lesion) reflects the abnormality level of a descriptor associated with said feature (and in particular the severity of the lesion).

In one embodiment, the abnormality level (in particular the severity of the lesion) is measured by comparison of the value of a descriptor associated with a feature with a reference value.

In one embodiment, the reference value may be an index value or may be derived from one or more risk prediction algorithms or computed indices for the presence and/or severity of a lesion or for prognosis or diagnosis. A reference value can be relative to a number or value derived from population studies, including, without limitation, such subjects having similar age range, subjects in the same or similar ethnic group, subjects having family histories of lesions within the organ, subjects affected by or not affected by a lesion within the organ or tissue or by a disease, or relative to the starting sample of a subject undergoing treatment for a lesion within the organ or tissue or for a disease. According to an embodiment, the reference population contains at least about 50, 75, 100, 200, 300, 400, 500 patients, preferably at least about 700 patients, more preferably at least about 1000 patients.

According to an embodiment, the reference population may be a population of patients affected with a liver disease, preferably with a hepatitis virus, preferably with the hepatitis C virus.

In one embodiment, a value of the descriptor associated with a feature inferior or equal to about 10%, 20%, 30%, 40%, 50%, 60%, 70%, 80%, 90%, 100% or more of the reference value, is indicative of an abnormality of said descriptor.

In one embodiment, a value of the descriptor associated with a feature superior or equal to about 10%, 20%, 30%, 40%, 50%, 60%, 70%, 80%, 90%, 100% or more of the reference value, is indicative of an abnormality of said descriptor.

In one embodiment, the reference value is a personalized reference, i.e. the reference value was determined using a sample obtained from the subject. According to an embodiment, a difference between the value of the descriptor associated with a feature superior and the personalized reference value is indicative of the appearance or disappearance of a lesion, or of an increased or a decreased severity of a pre-existing lesion, or is indicative of the presence or absence or of an increased or decreased severity of a disease.

In one embodiment of the present invention, the reference value is derived from the value obtained from a control sample derived from one or more subjects who are substantially healthy, i.e. who do not present lesion within their organ or tissue.

In another embodiment, a reference value can also be derived from the value in a sample derived from one or more subject who has been previously diagnosed or identified with a lesion in an organ or tissue or with a disease, or are at high risk for developing a lesion or a disease, or who have suffered from a lesion or from a disease.

According to one embodiment, the value may be positioned in a class of a classification which is set up in a reference population of patients with a lesion in an organ or a disease, such, as, for example, a reference population with a chronic liver disease. According to the invention, the presence and/or the severity of a lesion in an organ or of a disease may be assessed according to the class wherein the value has been classified.

According to another embodiment, the value may be positioned in a class of a classification which is set up in a reference population of substantially healthy patients, i.e. patients that do not present a lesion in an organ or a disease. According to the invention, the presence and/or the severity of a lesion in an organ or of a disease may be assessed according to the class wherein the value has been classified.

In one embodiment, the classification is based on quantiles, such as, for example, on quantiles of values (obtained by the patients of the reference population), or on quantiles of patients of the reference population.

In another embodiment, the classification is a previously described classification, based on a scoring system for a particular feature, preferably for a particular lesion.

In one embodiment, the classification correlates a specific value of the descriptor to an abnormality level of said descriptor (such as, for example, for a classification with 5 classes: normal, discrete abnormality, moderate abnormality, marked abnormality and severe abnormality).

In one embodiment, a color may be associated with each class of the classification. Therefore, according to this embodiment, the mask corresponding to a feature is colored according to the class of the classification wherein the value of a descriptor associated with said feature may be positioned.

In another embodiment, the highlighting step may correspond to the magnification of a feature associated with an abnormal descriptor, wherein the range of magnification may depend on the severity of the abnormality.

In a first embodiment of the invention, the method comprises:
  a) identifying a first feature on a medical image, generating a first mask corresponding to this feature and coloring the first mask in a first color,
  b) optionally identifying a second feature on the medical image, generating a second mask corresponding to this feature and coloring the second mask, preferably in a second color which is different from the first color,
  c) optionally repeating step (b), preferably every additional mask is colored in a different color, and
  d) displaying one easy-to-understand medical image.

In one embodiment, the method of the invention comprises displaying one easy-to-understand image resulting from the superimposition of all masks onto the medical image, thereby producing one modified medical image highlighting the first, and optionally second and additional features identified in steps (a) to (c), wherein each feature preferably appears in a different color.

In one embodiment, the method of the invention comprises displaying one easy-to-understand image resulting from the superimposition of all masks, thereby producing one medical image highlighting the first, and optionally second and additional features identified in steps (a) to (c), wherein each feature preferably appears in a different color.

Therefore, according to this embodiment, the superimposition of the at least one mask and optionally of the medical image is static, which means that all the features are highlighted in one single easy-to-understand image (wherein said easy-to-understand image results from the superimposition of masks or from the superimposition of masks and the medical image).

In a second embodiment of the invention, the method comprises:
  a) identifying a first feature on the medical image, generating a first mask corresponding to this feature, optionally coloring the first mask in a first color, and superimposing the first mask to the medical image, thereby producing a modified medical image highlighting the first feature, and
  b) optionally repeating step (a), thereby producing additional modified medical images each highlighting one additional feature,
  c) thereby producing a set of modified medical images each highlighting one feature identified in the medical image.

In a third embodiment of the invention, the method comprises:
  a) identifying a first feature on the medical image, generating a first mask corresponding to this feature, optionally coloring the first mask in a first color, thereby producing a first easy-to-understand medical image highlighting the first feature, and
  b) optionally repeating step (a), thereby producing additional easy-to-understand medical images each highlighting one additional feature,
  c) thereby producing a set of easy-to-understand medical images each highlighting one feature identified in the medical image.

In one embodiment, the visualization of the images of the set of images can be performed concomitantly (i.e. all images are displayed in separate views at the same time) or sequentially (i.e. images are displayed one by one).

In a fourth embodiment, the method of the invention comprises producing an easy-to-understand image highlighting all identified features, and additional images. Preferably, each additional image corresponds to an image of a set of easy-to-understand medical images each highlighting at least one feature (such as, for example, 1 or 2 or more) identified in the medical image. In one embodiment, each of these easy-to-understand images results from the superimposition of the mask corresponding to this or these feature(s) onto the medical image as described hereinabove. In another embodiment, each of these easy-to-understand images is a mask corresponding to at least one (such as, for example, 1 or 2 or more) feature(s) as described hereinabove.

In one embodiment, the visualization of the additional images can be performed either in separate images or in cartridge(s) close to the main image within the same view.

In one embodiment, the superimposition is sequential, and the method of the invention comprises:
  a. identifying a first feature on a medical image, generating a first mask corresponding to this feature, coloring the first mask in a first color, and superimposing the first mask onto the medical image, thereby producing a first modified medical image highlighting the first feature,
  b. identifying a second feature on the medical image, generating a second mask corresponding to this feature, coloring the second mask in a second color (preferably different from the first color), and superimposing the second mask onto the first modified medical image obtained in step (a), thereby producing a second modified medical image highlighting the first and second features,
  c. optionally repeating n times the step (b),
thereby producing a sequential set of modified medical image, wherein the image at position "n" in the sequential set highlights n features identified in steps (a) to (c), wherein each feature preferably appears in a different color.

In another embodiment, the superimposition is sequential, and the method of the invention comprises:
  a. identifying a first feature on the medical image, generating a first mask corresponding to this feature, coloring the first mask in a first color, thereby producing a first easy-to-understand medical image highlighting the first feature (wherein said first easy-to-understand medical image is the first mask),
  b. identifying a second feature on the medical image, generating a second mask corresponding to this feature, coloring the second mask in a second color (preferably different from the first color), and superimposing the second mask on the first easy-to-understand medical image obtained in step (a), thereby producing a second easy-to-understand medical image highlighting the first and second features,
  c. optionally repeating n times step (b),
thereby producing a sequential set of easy-to-understand medical image, wherein the image at position "n" in the sequential set highlights n features identified in steps (a) to (c), wherein each feature preferably appears in a different color.

In one embodiment, the method of the invention thus comprises displaying a set of at least 2 easy-to-understand images in the form of a slide show, wherein each image is displayed one after the other, preferably in a predetermined order and optionally with a predetermined period of time between each image display.

In one embodiment, each image in the position "n" of the slide show of the invention comprises the image at the position "n−1" and one or more additional mask(s) (preferably one additional mask) superimposed onto.

In one embodiment, the time between each image display is predetermined and ranges from about 0.5 seconds to about 1 minute, preferably from about 1 seconds to about 30 seconds, more preferably from about 3 seconds to about 15 seconds.

In another embodiment, each image display results from an action of a user (such as, for example, a patient or a physician visualizing the slide show), such as, for example, a mouse-click or the press of a button.

Therefore, according to these embodiments, the superimposition of the at least one mask optionally onto the medical image is dynamic, which means that masks are successively superimposed onto each other or onto the medical image, thereby resulting, according to these embodiments, to a slide show. In one embodiment, each feature successively (i.e. at different time but at the same location) appears on the easy-to-understand image, preferably in a predefined order, in order to progressively constitute the final easy-to-understand image. The successive appearance of each feature thus renders the medical image easy-to-understand.

In one embodiment, the method of the invention further comprises providing a medical report comprising the easy-to-understand image or the set of easy-to-understand images highlighting the features identified on the medical image, and optionally additional information as hereinabove described.

In one embodiment, the medical report is a printed paper. In another embodiment, the medical report is an electronic document or file or program, allowing visualizing the at least one easy-to-understand image on an electronic visualization means.

In one embodiment where a set of easy-to-understand images is provided, the predominance of each images may be adapted in the medical report. This means that a single image may be prominent according to the physician choice: e.g. only this image appears or only this image is colored. The predominance may also be a selected portion of the image highlighted in a separate image called cartridge where the image is modified, e.g. higher magnification.

In one embodiment where a set of easy-to-understand images is provided, the order of the images may be pre-defined.

In one embodiment where a set of easy-to-understand images is provided, one or more of these easy-to-understand images may be selected for appearing within the report, while others are excluded. This selection can be predefined or at the physician choice, e.g. by a click on the image of interest when the set of easy-to-understand images are provided in an electronic file.

In one embodiment, the medical report further comprises additional information regarding the medical image(s) and/or the easy-to-understand medical image(s), preferably in the form of a text. Examples of additional information include, but are not limited to, legend, description of the descriptors associated with a feature, value of a descriptor associated with a feature, level of abnormality of the feature or of the associated descriptor, importance of the lesion regarding the final diagnosis or staging and the like. Examples of annotated images are shown in FIGS. 11, 12 and 19 to 23.

In one embodiment, the additional information may appear as a unique legend linked to each easy-to-understand image of a set of easy-to-understand images.

In one embodiment, the additional information may appear as a legend for a complete set of easy-to-understand images. Then, the link between each easy-to-understand image and its corresponding legend is made by a direct link, like an arrow, or an indirect link like a code, preferably a descriptive typographic code, preferably a color code, e.g. the image A is colored in blue and the corresponding legend A is colored in blue.

In one embodiment, the legend may appear as a title, i.e. a text located inside the modified image or outside but close to the easy-to-understand image. In another embodiment, the legend may appear as a cartridge inserted within or outside the easy-to-understand image, the link between the feature and the legend being made either by a trait or arrow or a symbol like a star or a bullet.

In one embodiment of the invention, the method is computerized, which means that the image analysis is carried out by a computer, without the intervention of a human operator.

In another embodiment, the method is essentially computerized, which means that a human operator may intervene in some steps, such as, for example, for recovering the image or for removing artefacts on the medical image to be analyzed. However, the image analysis per se is computerized.

The present invention also relates to a device to perform the method of the invention, preferably to a microprocessor comprising a computer algorithm to perform the method of the invention.

The present invention also relates to a system comprising:
- a microprocessor comprising a computer algorithm to perform the method of the invention, and
- a visualizing means to present the at least one easy-to-understand medical images generated by the method of the invention.

EXAMPLES

The present invention is further illustrated by the following examples.

Example 1

Pathological Examination of Liver Fibrosis on Liver Biopsy

This example deals with pathological examination of liver fibrosis on liver biopsy in a human being with chronic C viral hepatitis and severe fibrosis (Metavir F3 stage).

Figure 1:
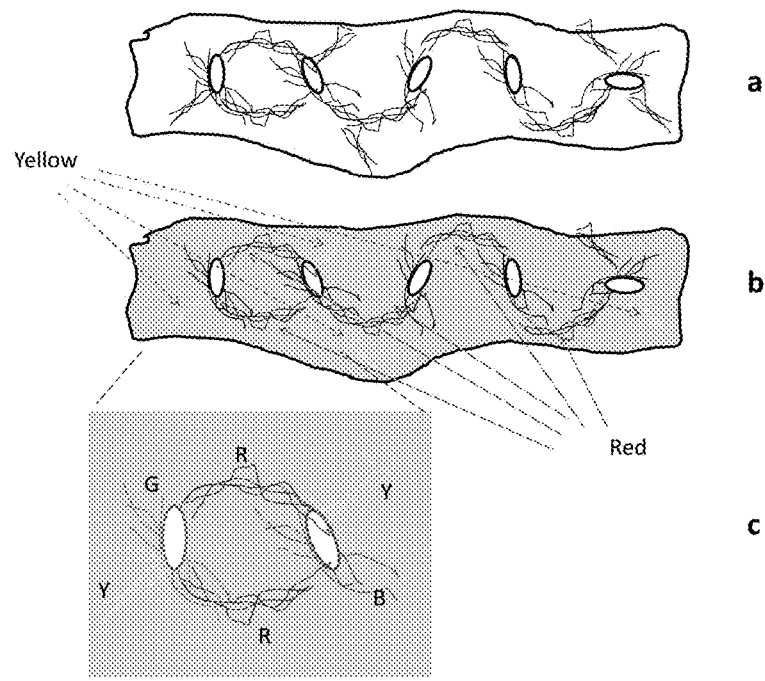
FIG. 1 is an overview of the method of the invention, applied on pathological examination of liver fibrosis on liver biopsy.

An overview of the method of the invention is depicted in FIG. 1. On Panel (a), fibrosis appears in black irregular fibrils within the image. On Panel (b), different components of liver fibrosis are highlighted: bridging fibrosis is depicted in red (R) and septa are depicted in yellow (Y). Colors are labeled only for compensating this black and white figure. Panel (c) shows details: the intensity of fibrosis in depicted in a liver lobule according to colored scale. Colors are labeled (Y: yellow, G: green, R: red, B: blue) only for this black and white figure.

Figure 2:
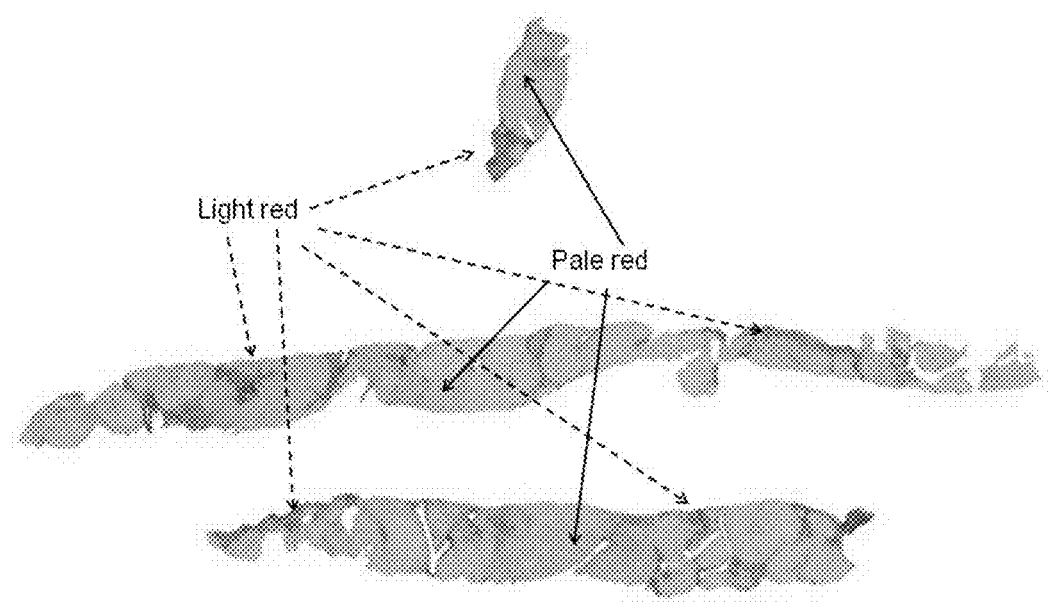
FIG. 2 is an optical image of whole liver biopsy material after fixation, section and coloration (staining) with picrosirius red (dark parts in this black and white figure).

An optical image of a liver biopsy from a patient with severe fibrosis (Metavir F3 stage) was recovered after fixation, section and staining using picrosirius red. Picrosirius red staining allows visualization of collagen fibers. However, as shown in FIG. 2 and FIG. 3, a non-expert cannot distinguish fibrosis on such an optical image, even after selection of a region of interest on said optical image.

Figure 4:
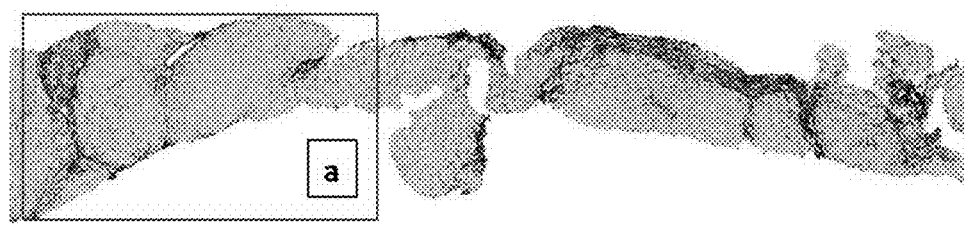
FIG. 4 is an image corresponding to FIG. 3 panel C (number of superimposed images: 2). Total fibrosis appears here in intense black. Total fibrosis is a composite image obtained by automated algorithm and superimposed on liver specimen background (grey parts). The cartridge (a) selects the new region of interest.
Figure 13:
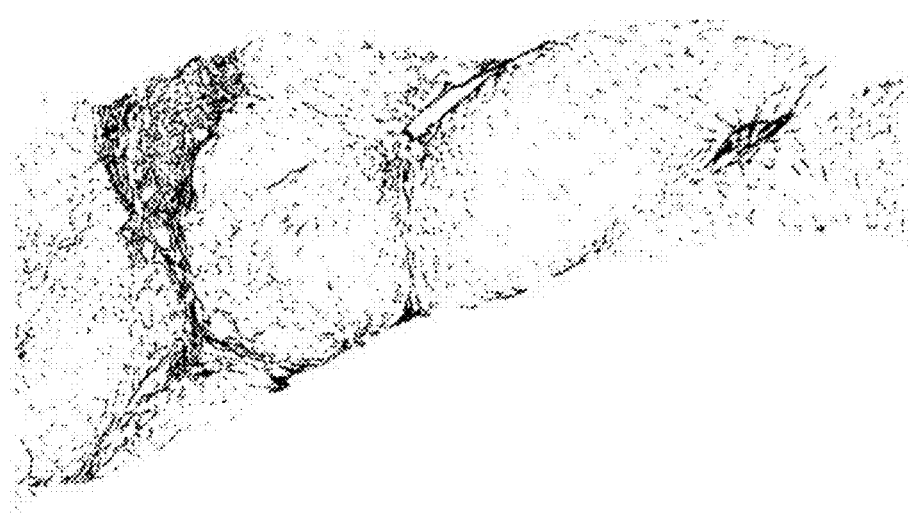
FIG. 13 is a mask of total fibrosis, wherein fibrosis appears in black, while the rest of liver biopsy is in white.

Using the method of the invention, an automated algorithm is applied to obtain a mask corresponding to total fibrosis: on this mask, total fibrosis appears in black, while background is in white (FIG. 13). The total fibrosis mask is then superimposed on the previous optical image, thereby obtaining a modified image highlighting total fibrosis. As shown in FIG. 4, a non-expert can now easily distinguish fibrosis (in black) from the background (in grey). However, it is not possible to distinguish the components of fibrosis on this image.

Figure 3:
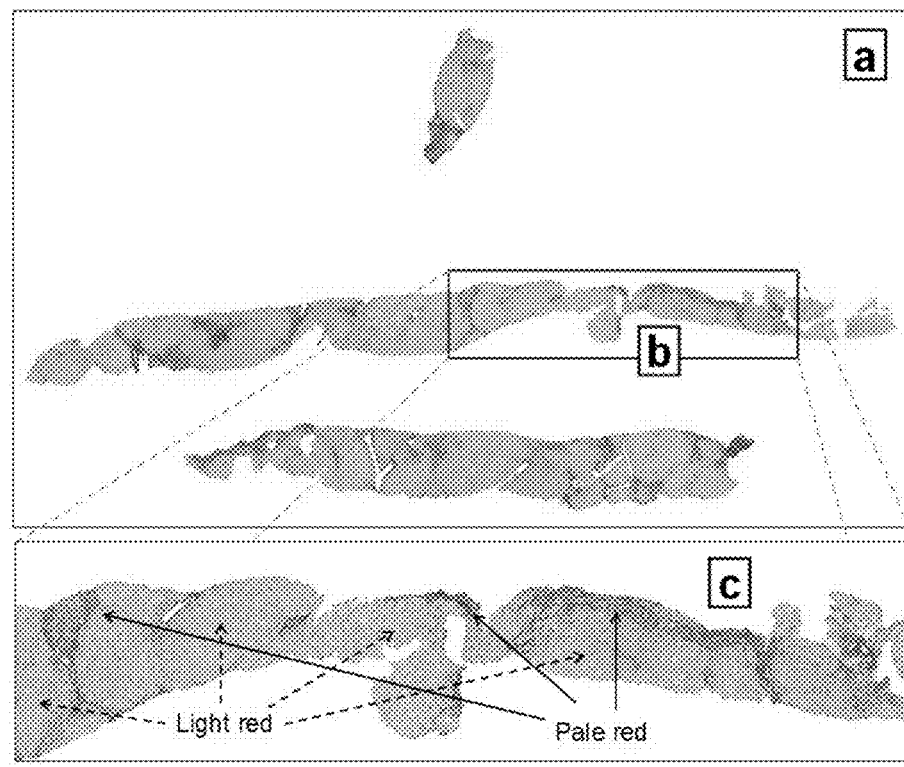
FIG. 3 is an optical image of whole liver biopsy material. Panel (a): whole material as in FIG. 2. Panel (b): the cartridge selects the region of interest. Panel (c): the region of interest appears in higher magnification and fibrosis colored in pale red is more visible while the background appears in light red (dark parts in this black and white figure).
Figure 5:
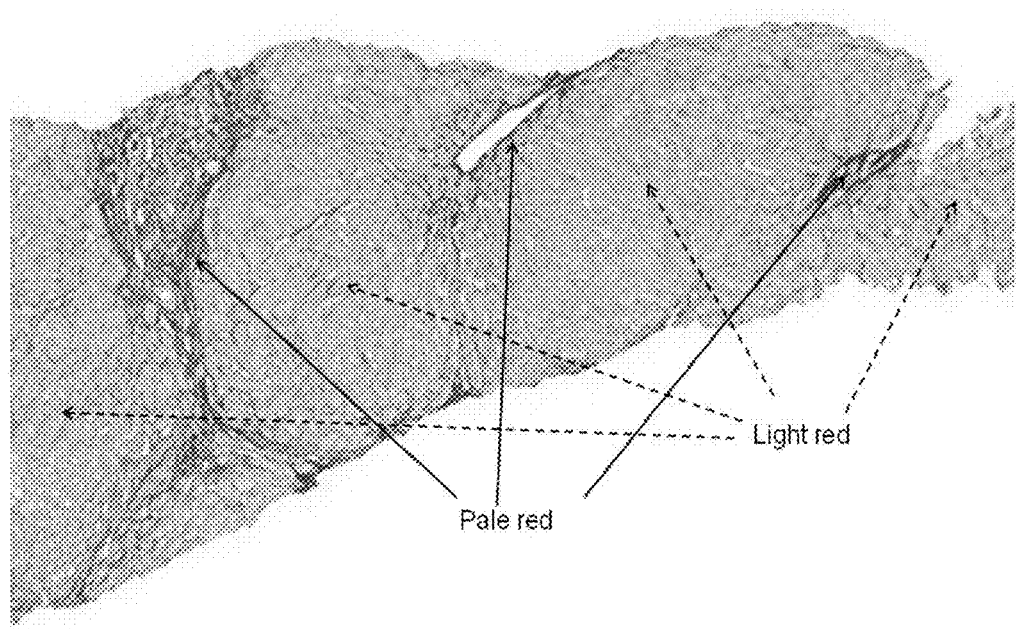
FIG. 5 is an image corresponding to FIG. 3 cartridge (C) at a higher magnification but without component selection by the method of the invention.

In order to distinguish the different components of fibrosis, an image corresponding to FIG. 3 panel (C) with higher magnification may be used (FIG. 5).

Figure 6:
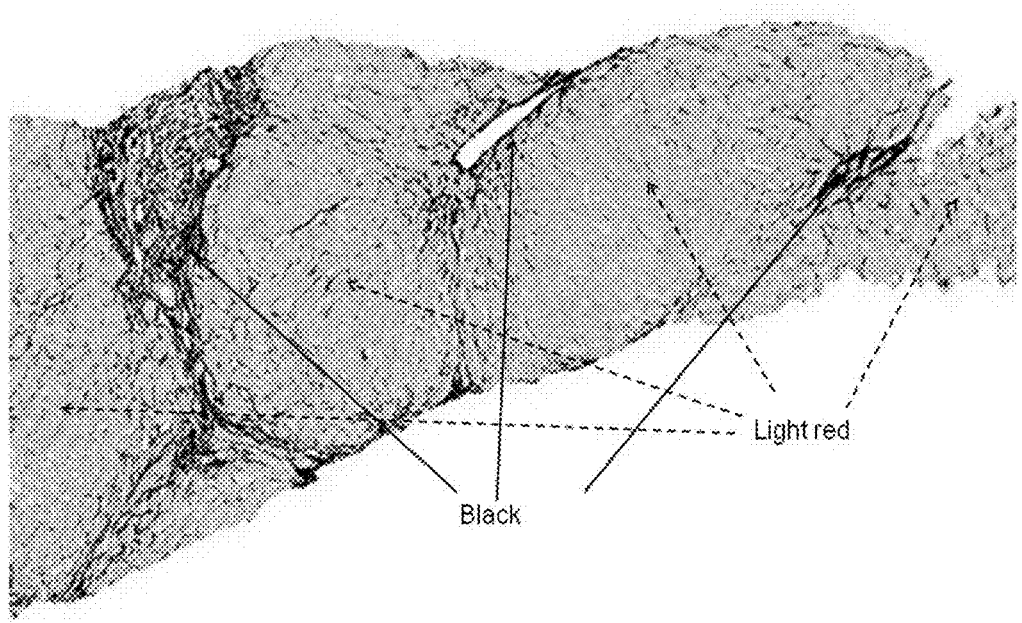
FIG. 6 is an image corresponding to FIG. 5 wherein total fibrosis is highlighted using the method of the invention. Total fibrosis appears in black. Total fibrosis is a composite image obtained by automated algorithm: this mask is superimposed on liver specimen background in light red (grey parts in this black and white figure).

From this image, a mask of total fibrosis is obtained as described above and superimposed on liver specimen background in grey. The superimposition of these 2 images thus result in a novel image highlighting total fibrosis (FIG. 6).

Figure 7:
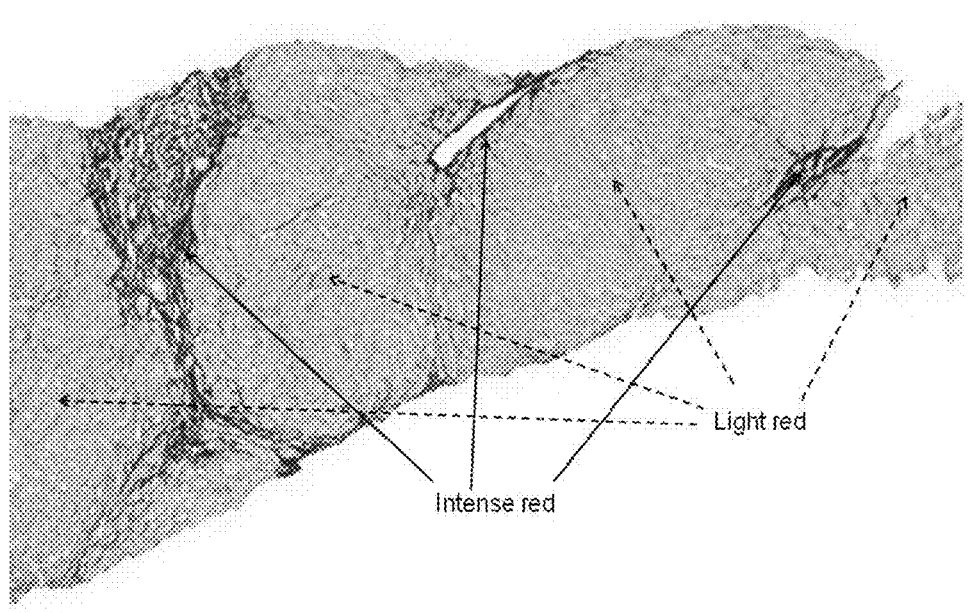
FIG. 7 is an image corresponding to FIG. 5 wherein porto-septal fibrosis is highlighted using the method of the invention. Porto-septal fibrosis appears in intense red (black parts in this black and white figure). Porto-septal fibrosis is a composite image obtained by automated algorithm: this mask is superimposed on liver specimen background in light red (grey parts in this black and white figure).
Figure 14:
FIG. 14 is a mask of porto-septal fibrosis, wherein porto-septal fibrosis appears in intense red (black in the black and white image), while the rest of liver biopsy is in white.

From the image of FIG. 5, a second mask corresponding to porto-septal fibrosis is obtained using the automated algorithm of the invention: on this mask, porto-septal fibrosis appears in intense red in this example, while background is in white (FIG. 14). The porto-septal fibrosis mask is then superimposed on liver specimen background in grey. The superimposition of these 2 images thus results in a novel image highlighting porto-septal fibrosis (FIG. 7).

Figure 8:
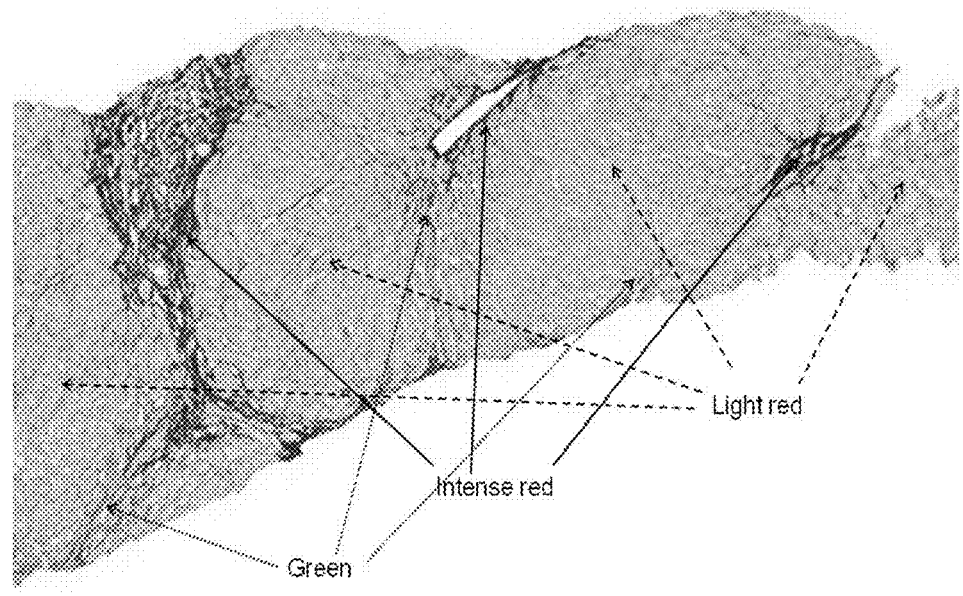
FIG. 8 is an image corresponding to FIG. 5 wherein perisinusoidal fibrosis and porto-septal fibrosis are highlighted using the method of the invention. Perisinusoidal fibrosis appears in green (dark grey parts in this black and white figure). Porto-septal fibrosis appears in intense red (black parts in this black and white figure). Perisinusoidal fibrosis and porto-septal fibrosis are composite images obtained by automated algorithm: these masks are superimposed on liver specimen background in light red (grey parts in this black and white figure).
Figure 15:
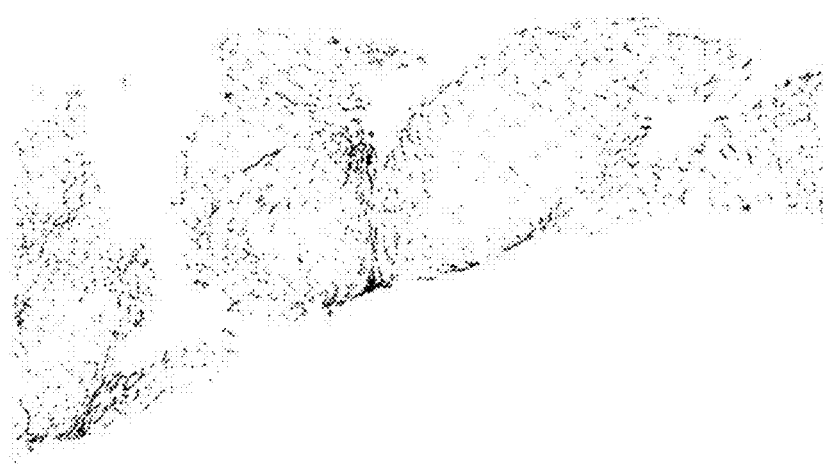
FIG. 15 is a mask of perisinusoidal fibrosis, wherein perisinusoidal fibrosis appears in green (black in the black and white image), while the rest of liver biopsy is in white.

From the image of FIG. 5, a third mask corresponding to perisinusoidal fibrosis is obtained using the automated algorithm of the invention: on this mask, perisinusoidal fibrosis appears in green in this example, while background is in white (FIG. 15). The perisinusoidal fibrosis mask is then superimposed on liver specimen background in grey. The superimposition of these 2 images thus results in a novel image highlighting perisinusoidal fibrosis. In a further step, the porto-septal mask described above is superimposed to the image highlighting perisinusoidal fibrosis, thereby obtaining a novel image highlighting and distinguishing porto-septal and perisinusoidal fibrosis (FIG. 8). This novel image thus results from the superimposition of 3 images (magnified medical image and two masks).

Figure 9:
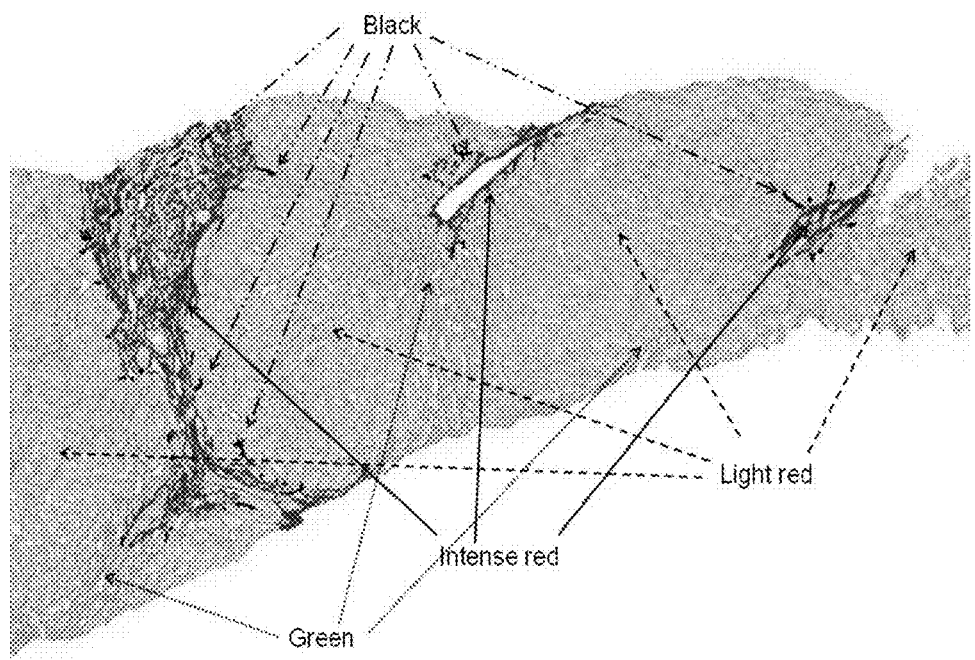
FIG. 9 is an image corresponding to FIG. 5 wherein perisinusoidal fibrosis, portal fibrosis and stellar fibrosis are highlighted using the method of the invention. Compared to FIG. 8, porto-septal fibrosis is distinguished in its two main components: portal fibrosis appears in intense red and stellar fibrosis appears in black (both in black parts in this black and white figure). Perisinusoidal fibrosis appears in green (dark grey parts in this black and white figure). Perisinusoidal, portal and stellar fibrosis are composite images (masks) obtained by automated algorithms and superimposed on liver specimen background in pale red (grey parts in this black and white figure).
Figure 16:
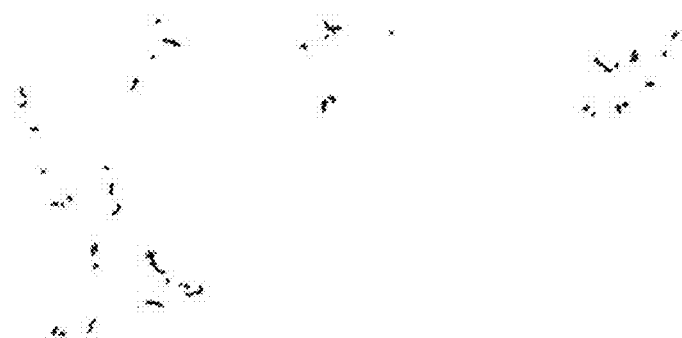
FIG. 16 is a mask of stellar fibrosis, wherein stellar fibrosis appears in black, while the rest of liver biopsy is in white.

The two main components of porto-septal fibrosis are portal fibrosis and stellar fibrosis. In order to distinguish these two components, two masks are obtained using the automated algorithm of the invention. The first mask corresponds to portal fibrosis: on this mask, portal fibrosis appears in intense red, while background is in white. The second mask corresponds to stellar fibrosis: on this mask, stellar fibrosis appears in black, while background is in white (FIG. 16). The superimposition of the portal fibrosis mask and of the stellar fibrosis mask superimposed on liver specimen background in grey result in a novel image highlighting both portal fibrosis and stellar fibrosis, wherein both portal fibrosis and stellar fibrosis may be easily distinguished. In a further step, the perisinusoidal mask described above is superimposed to the image highlighting both portal fibrosis and stellar fibrosis, thereby obtaining a novel image highlighting and distinguishing portal fibrosis, stellar fibrosis and perisinusoidal fibrosis (FIG. 9). This novel image thus results from the superimposition of 4 images (magnified medical image and three masks).

Figure 17:
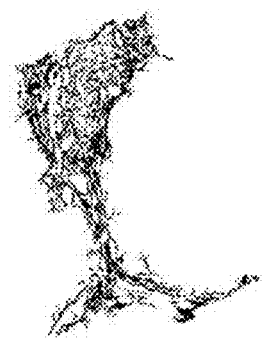
FIG. 17 is a mask of bridging fibrosis, wherein bridging fibrosis appears in magenta (black in the black and white image), while the rest of liver biopsy is in white.

Portal fibrosis may be distinguished into bridging fibrosis and simple septa. Bridging fibrosis is a characteristic of Metavir F3 stage (severe fibrosis). In order to distinguish these two components, two masks are obtained using the automated algorithm of the invention. The first mask corresponds to bridging fibrosis: on this mask, bridging fibrosis appears in magenta, while background is in white (FIG. 17). The second mask corresponds to simple septa: on this mask, simple septa appears in red, while background is in white. The superimposition of the bridging fibrosis mask and of the simple septa mask superimposed on liver specimen background in grey result in a novel image highlighting both bridging fibrosis and simple septa, wherein both bridging fibrosis and simple septa may be easily distinguished. In a further step, the perisinusoidal mask described above is superimposed to the image highlighting both bridging fibrosis and simple septa, thereby obtaining a novel image highlighting and distinguishing bridging fibrosis, simple septa and perisinusoidal fibrosis. This novel image thus results from the superimposition of 4 images (magnified medical image and three masks).

Figure 10:
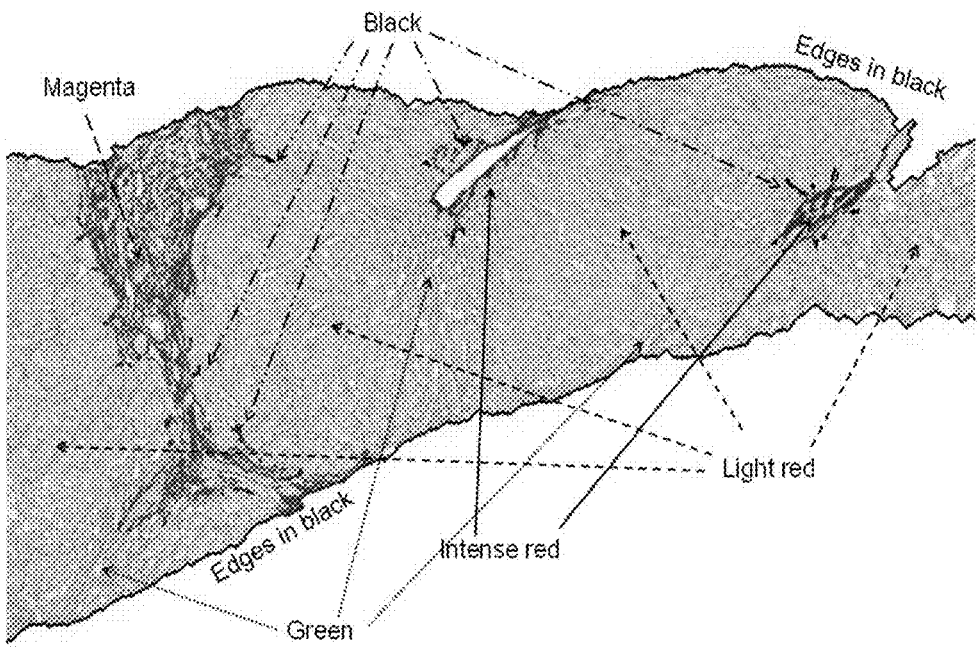
FIG. 10 is an image corresponding to FIG. 5 wherein perisinusoidal fibrosis, bridging fibrosis, simple septa, stellar fibrosis and edges of the liver biopsy are highlighted using the method of the invention. Stellar fibrosis appears in black. Bridging fibrosis appears in magenta (dark grey) and simple septa appears in red (light black parts). Perisinusoidal fibrosis appears in green (dark grey parts in this black and white figure). Perisinusoidal, portal, bridging and stellar fibrosis are composite images (masks) obtained by automated algorithms and superimposed on liver specimen background in pale red (light grey parts in this black and white figure). Edges of the liver biopsy appear in black.
Figure 18:
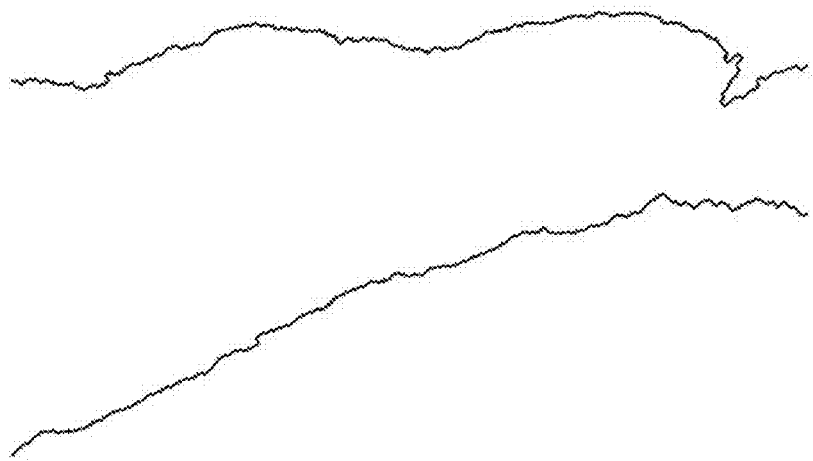
FIG. 18 is a mask of liver biopsy edges, wherein liver biopsy edges appear in black, while the rest of liver biopsy is in white.

Moreover, a mask corresponding to the edges of the liver biopsy is obtained by the automated method of the invention: on said mask, edges of the liver biopsy appear in black, while the rest of the liver biopsy is in white (FIG. 18). Said edge mask may then be superimposed to the image highlighting and distinguishing bridging fibrosis, simple septa and perisinusoidal fibrosis, thereby obtaining a novel image resulting from the superimposition of 5 images (magnified medical image and four masks, FIG. 10).

Figure 11:
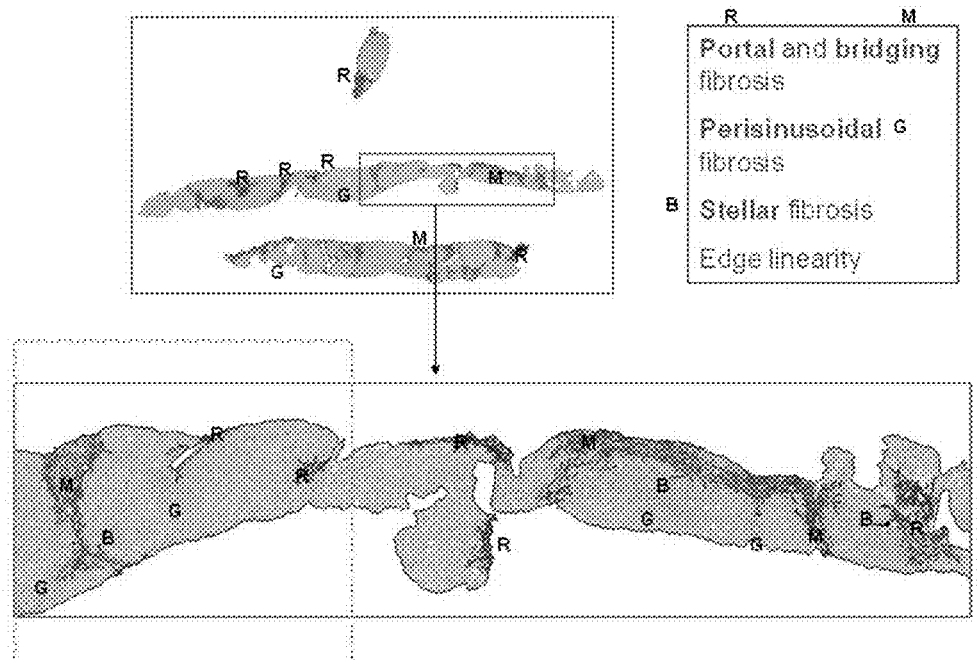
FIG. 11 is a cumulative image on whole liver material with legend. The dashed cartridge indicates the region of interest. Colors are labeled (M: magenta, G: green, R: red, B: blue) only for this black and white figure.
Figure 12:
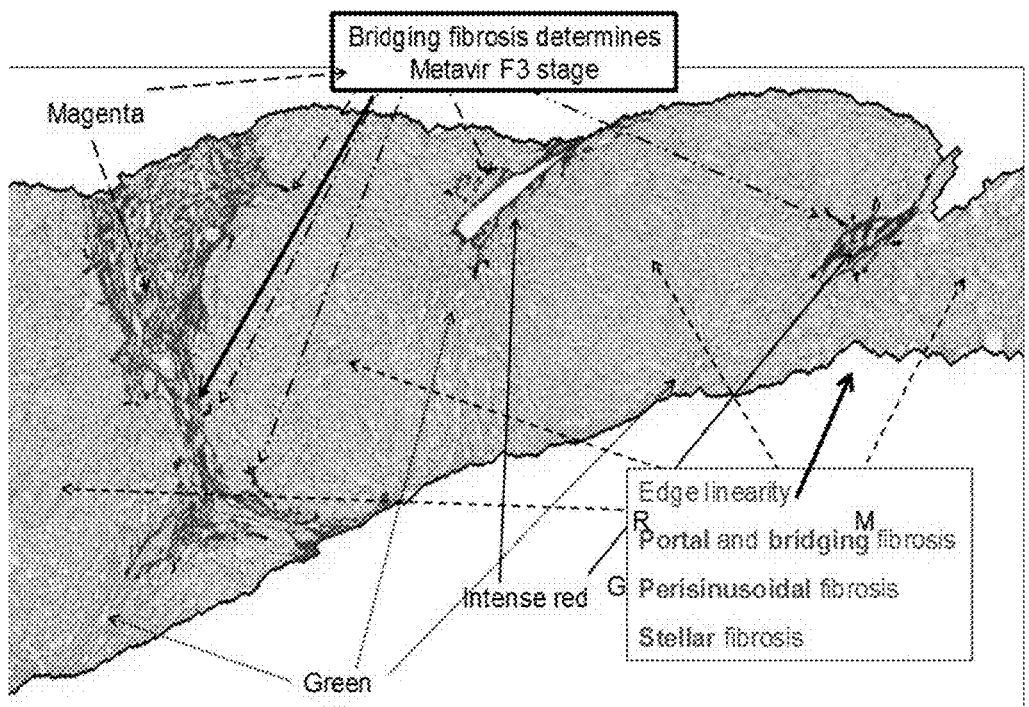
FIG. 12 is a cumulative image on region of interest (masks) selected in previous figures with detailed and located legends. Only the large arrows appear in a real coloured view.

Examples of final imaged report that may be obtained by the method of the invention are shown in FIGS. 11 and 12.

Example 2

Radiological Examination of Liver Fibrosis on Liver CT-scan

This example deals with radiological examination of liver fibrosis on liver CT-scan in human beings with chronic viral hepatitis C.

Figure 19:
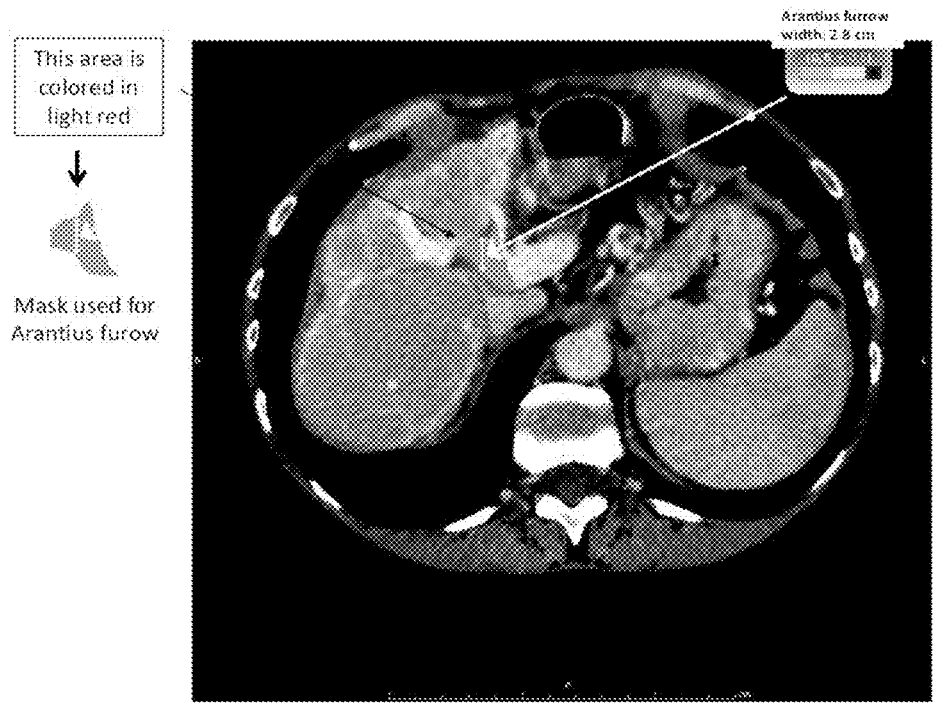
FIG. 19 is a modified image obtained by the method of the invention, wherein Arantius furrow is highlighted.

In a first example, an image is recovered from a cirrhotic (Metavir F4) patient with large Arantius furrow. The method of the invention comprises automatically generating a mask corresponding to Arantius furrow: in this mask, the surface of Arantius furrow appears in black, while the rest of the image is in white. The Arantius furrow mask is then colored according to the abnormality scoring of Arantius furrow width. In this example, the mask is colored in light red, thereby highlighting a high but not maximal score of abnormality. Said colored Arantius furrow mask is then superimposed to the medical image, thereby obtaining a novel image resulting from the superimposition of the mask and the medical image and highlighting Arantius furrow (medical image and one mask, FIG. 19). In the report obtained by the method of the invention, the mask on the left part, which is the mask superimposed on the medical image, may or may not appear. In this example, a cartridge includes the descriptor name, the range of normality of the descriptor and the abnormality scoring (blue/orange/red).

Figure 20:
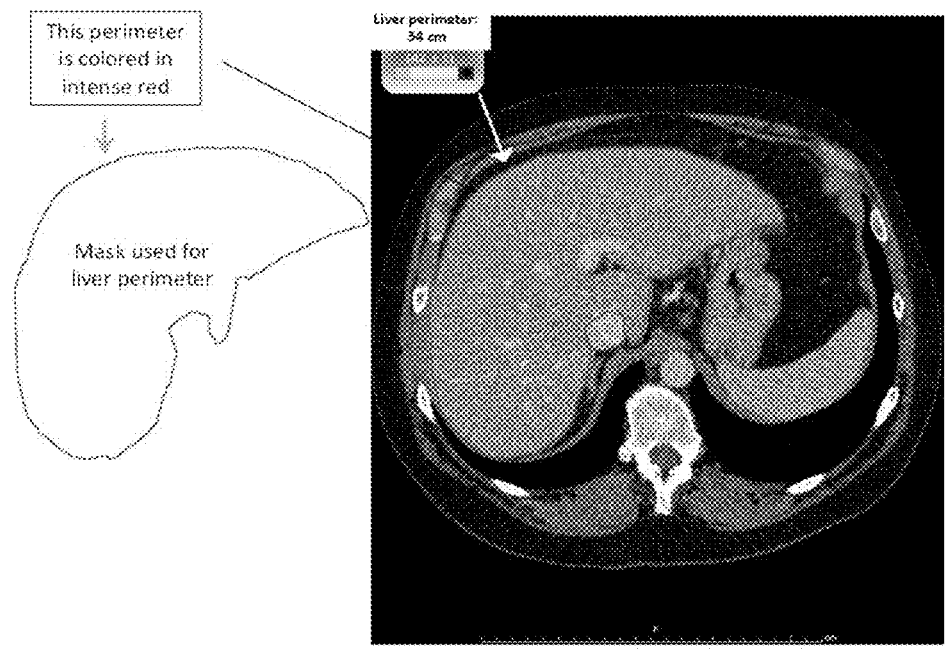
FIG. 20 is a modified image obtained by the method of the invention, wherein liver perimeter is highlighted.

In a second example, an image is recovered from a cirrhotic (Metavir F4) patient with large liver perimeter. The method of the invention comprises automatically generating a mask corresponding to the liver perimeter: in this mask, the contour of the liver (liver perimeter) appears in black, while the rest of the image is in white. The liver perimeter mask is then colored according to the abnormality scoring of the liver perimeter. In this example, the mask is colored in intense red, thereby highlighting a high score of abnormality. Said colored liver perimeter mask is then superimposed to the medical image, thereby obtaining a novel image resulting from the superimposition of 2 images and highlighting liver perimeter (medical image and one mask, FIG. 20). In the report obtained by the method of the invention, the mask on the left part, which is the mask superimposed on the medical image, may or may not appear. In this example, a cartridge includes the descriptor name, the range of normality of the descriptor and the abnormality scoring (blue/orange/red).

Figure 21:
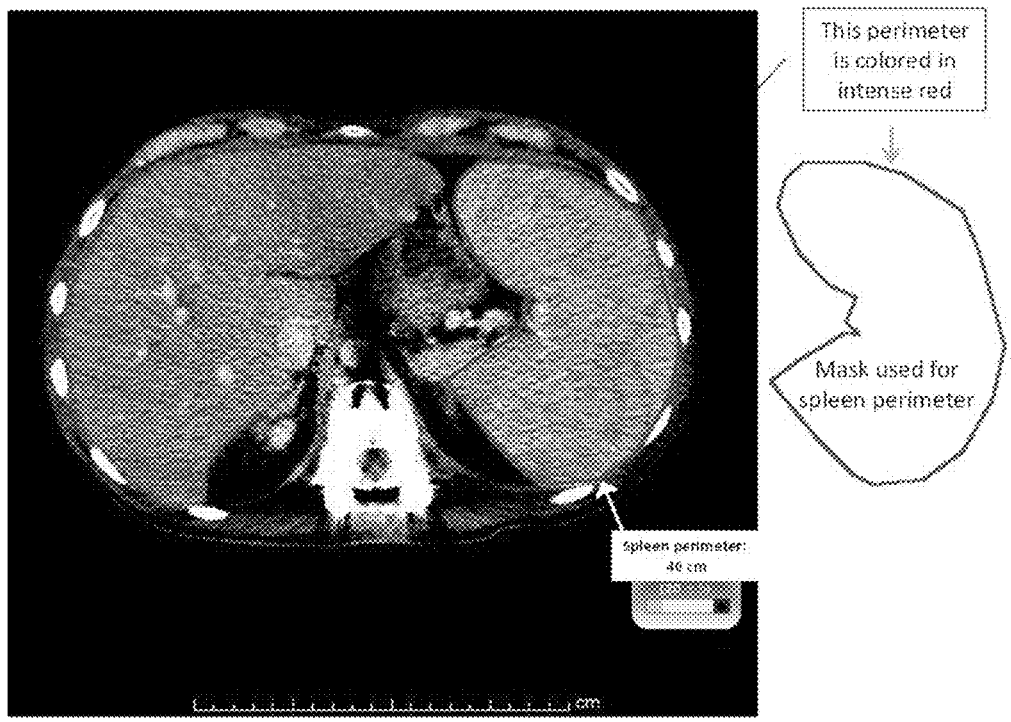
FIG. 21 is a modified image obtained by the method of the invention, wherein spleen perimeter is highlighted.

In a third example, an image is recovered from a cirrhotic (Metavir F4) patient with large spleen perimeter. The method of the invention comprises automatically generating a mask corresponding to the spleen perimeter: in this mask, the contour of the spleen (spleen perimeter) appears in black, while the rest of the image is in white. The spleen perimeter mask is then colored according to the abnormality scoring of the spleen perimeter. In this example, the mask is colored in intense red, thereby highlighting a high score of abnormality. Said colored spleen perimeter mask is then superimposed to the medical image, thereby obtaining a novel image resulting from the superimposition of 2 images and highlighting spleen perimeter (medical image and one mask, FIG. 21). In the report obtained by the method of the invention, the mask on the right part, which is the mask superimposed on the medical image, may or may not appear.

In this example, a cartridge includes the descriptor name, the range of normality of the descriptor and the abnormality scoring (blue/orange/red).

Figure 22:
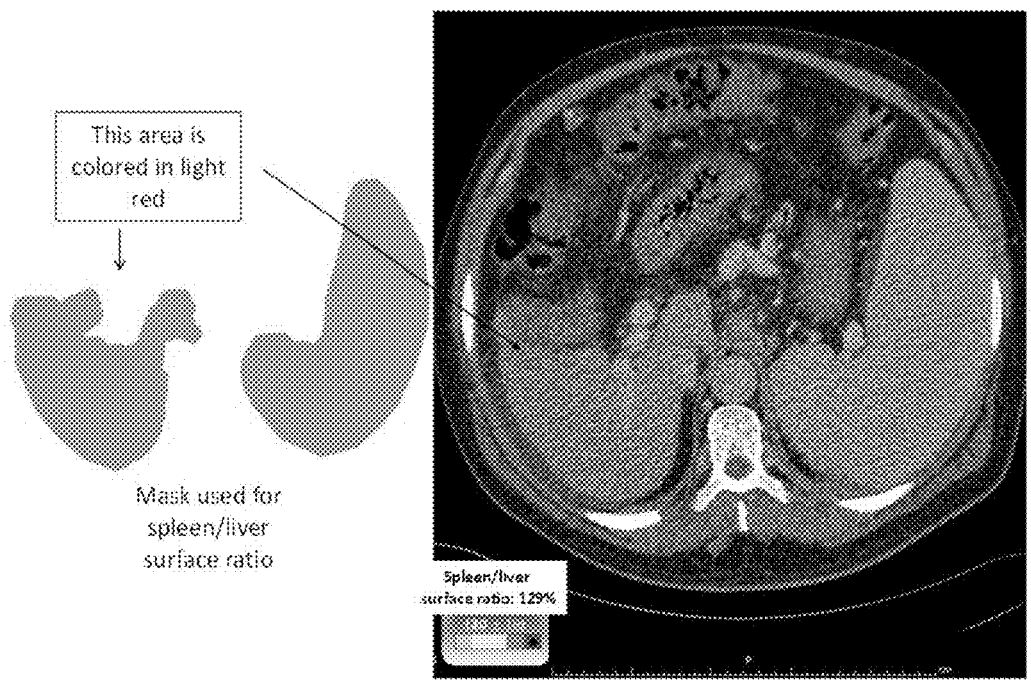
FIG. 22 is a modified image obtained by the method of the invention, wherein spleen surface and liver surface are highlighted.

In a fourth example, an image is recovered from a cirrhotic (Metavir F4) patient with high liver/spleen surface ratio. The method of the invention comprises automatically generating a mask corresponding to both the liver surface and the spleen surface: in this mask, the surface of the spleen and the surface of the liver appear in black, while the rest of the image is in white. This mask is then colored according to the abnormality scoring of the ratio liver surface/spleen surface. In this example, the mask is colored in light red, thereby highlighting a high but not maximal score of abnormality of the ratio liver surface/spleen surface. Said colored mask is then superimposed to the medical image, thereby obtaining a novel image resulting from the superimposition of 2 images and highlighting liver surface and spleen surface (medical image and one mask, FIG. 22). In the report obtained by the method of the invention, the mask on the left part, which is the mask superimposed on the medical image, may or may not appear. In this example, a cartridge includes the descriptor name, the range of normality of the descriptor and the abnormality scoring (blue/orange/red).

Figure 23:
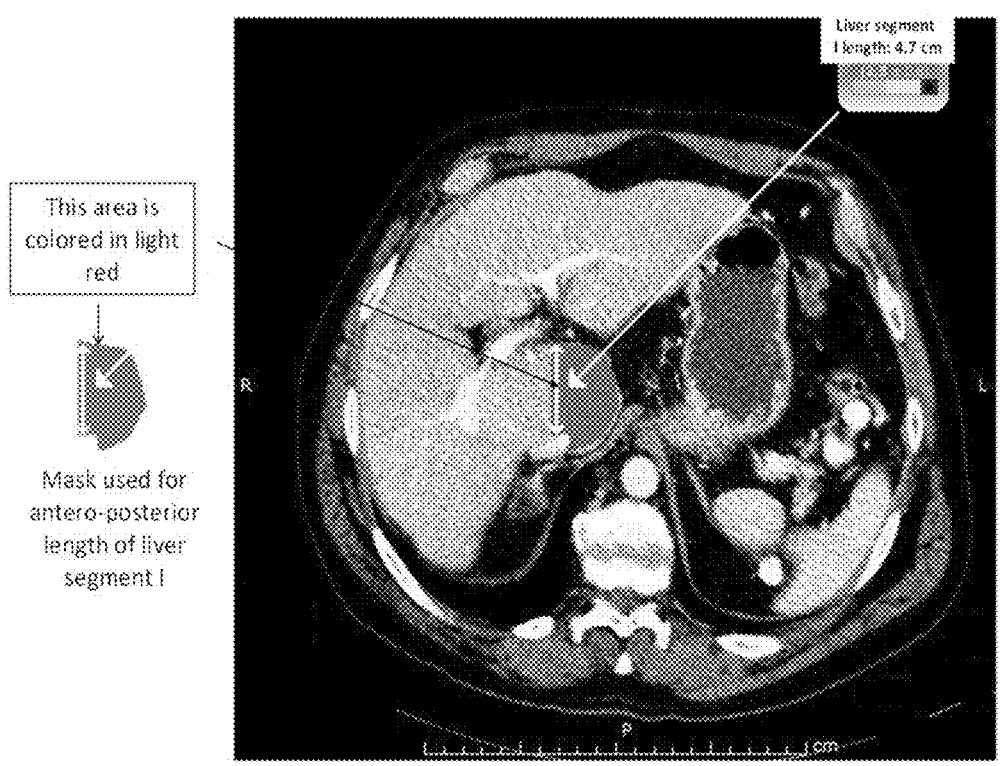
FIG. 23 is a modified image obtained by the method of the invention, wherein liver segment I surface is highlighted.
Figure 24:
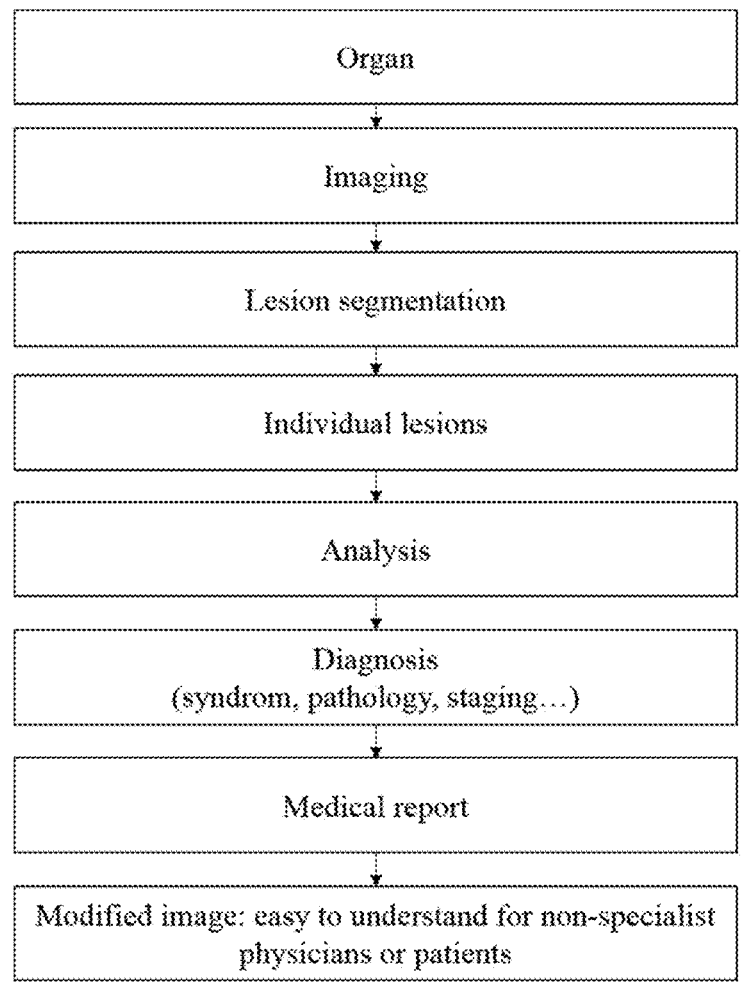
FIG. 24 is a diagram illustrating the successive steps of an embodiment of the method of the invention.

In a fifth example, a medical image is recovered from a cirrhotic (Metavir F4) patient with large antero-posterior length of liver segment I. The method of the invention comprises automatically generating a mask corresponding to the liver segment I: in this mask, the surface of the liver segment I appears in black, while the rest of the image is in white. This mask is then colored according to the abnormality scoring of the length of the antero-posterior liver segment I. In this example, the mask is colored in intense red, thereby highlighting a high score of abnormality of the length of the antero-posterior liver segment I. Said colored mask is then superimposed to the medical image, thereby obtaining a novel image resulting from the superimposition of 2 images and highlighting the surface of the liver segment I (medical image and one mask, FIG. 23). In the report obtained by the method of the invention, the mask on the left part, which is the mask superimposed on the medical image, may or may not appear. In this example, a cartridge includes the descriptor name, the range of normality of the descriptor and the abnormality scoring (blue/orange/red).

The invention claimed is:

1. A method for displaying at least two medical images, each medical image highlighting at least one feature, said method comprising the steps of:
  a) obtaining at least one 2D medical image of whole or part of the liver of a subject;
  b) identifying on the medical image of step a) at least two features;
  c) generating masks showing the features of step b), each mask highlighting at least one feature identified in step b), wherein said masks are selected from total fibrosis mask, porto-septal fibrosis mask, perisinusoidal fibrosis mask, portal fibrosis mask, stellar fibrosis mask, bridging fibrosis mask, simple septa mask, biopsy edge mask, biopsy specimen surface mask, Arantius furrow perimeter mask, Arantius furrow surface mask, liver perimeter mask, liver surface mask, spleen perimeter mask, spleen surface mask, liver segment I perimeter mask, liver segment IV perimeter mask, liver segment IV surface mask, liver and spleen surfaces mask and liver and spleen perimeters mask;
  d) generating a set of at least two medical images, each medical image highlighting at least one feature identified in step b), by superimposing at least one mask of step c) on the medical image of step a); and
  displaying the set of at least two medical images of step d), one after the other;
  wherein an automated algorithm is used in step b) for identifying the features of step b) and for generating the masks of step c).

2. The method according to claim 1, wherein the medical image of step a) is an image recovered by radiology, anatomy, pathology, histo-pathology, anatomo-pathology, cytology, nuclear medicine, endoscopy or biology.

3. The method according to claim 1, wherein the features are:
  a lesion, selected from the group comprising whole fibrosis, bridging fibrosis, septa, porto-septal fibrosis, perisinusoidal fibrosis, portal fibrosis or stellar fibrosis, or
  a morphometric data, selected from the group comprising perimeter of an organ or fragment thereof and surface of an organ or fragment thereof.

4. The method according to claim 1, wherein the features are perisinusoidal fibrosis and porto-septal fibrosis.

5. The method according to claim 1, wherein the features are perisinusoidal fibrosis, portal fibrosis and stellar fibrosis.

6. The method according to claim 1, further comprising:
  identifying a first feature on the medical image, generating a first mask corresponding to this feature and coloring the first mask in a first color;
  identifying a second feature on the medical image, generating a second mask corresponding to this feature and coloring the second mask in a second color which is different from the first color; and
  superimposing the masks onto the medical image,
  thereby producing a medical image highlighting the said features, wherein each feature appears in a different color.

7. The method according to claim 1, further comprising:
  identifying a first feature on the medical image, generating a first mask corresponding to this feature and coloring the first mask in a first color;
  identifying a second feature on the medical image, generating a second mask corresponding to this feature and coloring the second mask in a second color which is different from the first color;
  repeating the previous step, wherein every additional mask is colored in a different color; and
  superimposing the masks onto the medical image,
  thereby producing a medical image highlighting the said features, wherein each feature appears in a different color.

8. The method according to claim 1, further comprising:
  identifying a first feature on the medical image, generating a first mask corresponding to this feature, and superimposing the first mask onto the medical image, thereby producing a first medical image highlighting the first feature; and
  repeating the previous step, thereby producing additional medical images each highlighting one additional feature,
  thereby producing a set of medical images wherein each image highlights one feature.

9. The method according to claim 1, wherein said method further comprises measuring at least one descriptor on the medical image.

10. The method according to claim 1, wherein said method further comprises measuring at least one descriptor on the medical image, said descriptor being selected from fractal dimension of porto-septal fibrosis, fractal dimension of perisinusoidal fibrosis, ratio of perisinusoidal fibrosis area, whole area of stellar fibrosis, portal area of stellar fibrosis, mean portal distance, number of bridges, portal ratio of the bridges, mean bridge thickness, mean granularity percentage, mean nodularity percentage, fragmentation index, edge linearity percentage, density heterogeneity, Arantius furrow width, mean liver perimeter, mean spleen perimeter, ratio of spleen to liver surface, frontal or sagittal length of liver segment I, and whole spleen perimeter.

11. The method according to claim 1, wherein the color of the mask highlighting a feature reflects the abnormality level of a descriptor associated with said feature.

12. The method according to claim 1, wherein the feature is a lesion and wherein the color of the mask highlighting said lesion reflects the severity of the lesion.

13. The method according to claim 1, wherein the set of at least two images further comprises a legend or additional information.

14. The method according to claim 1, wherein the method is computerized.

15. A microprocessor, comprising a memory having program code stored thereon that embodies a computer algorithm that, upon execution by the microprocessor, causes the microprocessor to perform the method according to claim 1.

16. A system, comprising:
 a microprocessor according to claim 15; and
 a visualizing means to present the set of at least two medical images.

* * * * *